(12) United States Patent
Staskin et al.

(10) Patent No.: US 8,777,836 B2
(45) Date of Patent: Jul. 15, 2014

(54) PELVIC HEALTH IMPLANTS AND METHODS

(75) Inventors: David R. Staskin, New York, NY (US); Kimberly A. Anderson, Eagan, MN (US); Karen Pilney Montpetit, Mendota Heights, MN (US); John W. Westrum, Jr., Prior Lake, MN (US); Brian P. Watschke, Eden Prairie, MN (US); James E. Cox, Corcoran, MN (US)

(73) Assignee: AMS Research Corporation, Minnetonka, MN (US)

( * ) Notice: Subject to any disclaimer, the term of this patent is extended or adjusted under 35 U.S.C. 154(b) by 1955 days.

(21) Appl. No.: 11/983,430

(22) Filed: Nov. 7, 2007

(65) Prior Publication Data

US 2008/0140218 A1 Jun. 12, 2008

Related U.S. Application Data

(63) Continuation of application No. 10/423,662, filed on Apr. 25, 2003, now Pat. No. 7,407,480, which is a continuation-in-part of application No. 09/917,443, filed on Jul. 27, 2001, now Pat. No. 6,612,977, and a continuation-in-part of application No. 10/280,341, filed on Oct. 25, 2002, now Pat. No. 6,971,986.

(60) Provisional application No. 60/380,591, filed on May 15, 2002, provisional application No. 60/456,750, filed on Mar. 21, 2003.

(51) Int. Cl.
*A61F 2/00* (2006.01)

(52) U.S. Cl.
USPC .................................. 600/37; 600/30

(58) Field of Classification Search
USPC .................. 600/29, 30, 37; 128/897, 898
See application file for complete search history.

(56) References Cited

U.S. PATENT DOCUMENTS

| | | |
|---|---|---|
| 2,738,790 A | 3/1956 | Todt et al. |
| 3,124,136 A | 3/1964 | Usher |
| 3,182,862 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |

(Continued)

FOREIGN PATENT DOCUMENTS

| | | |
|---|---|---|
| DE | 2305815 | 2/1973 |
| DE | 4220283 C2 | 5/1994 |

(Continued)

OTHER PUBLICATIONS

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

(Continued)

*Primary Examiner* — Samuel Gilbert
(74) *Attorney, Agent, or Firm* — Kagan Binder, PLLC

(57) ABSTRACT

Surgical articles, implants and components suitable for female pelvic health procedures are described.

5 Claims, 24 Drawing Sheets

(56) References Cited

U.S. PATENT DOCUMENTS

| | | | |
|---|---|---|---|
| 3,858,783 A | 1/1975 | Kapitanov et al. | |
| 3,924,633 A | 12/1975 | Cook et al. | |
| 3,995,619 A | 12/1976 | Glatzer | |
| 4,019,499 A | 4/1977 | Fitzgerald | |
| 4,037,603 A | 7/1977 | Wendorff | |
| 4,128,100 A | 12/1978 | Wendorff | |
| 4,172,458 A | 10/1979 | Pereyra | |
| 4,235,238 A | 11/1980 | Ogiu et al. | |
| 4,246,660 A | 1/1981 | Wevers | |
| 4,441,497 A | 4/1984 | Paudler | |
| 4,509,516 A | 4/1985 | Richmond | |
| 4,632,100 A | 12/1986 | Somers et al. | |
| 4,775,380 A | 10/1988 | Seedhom et al. | |
| 4,857,041 A | 8/1989 | Annis et al. | |
| 4,865,031 A | 9/1989 | O'Keeffe | |
| 4,920,986 A | 5/1990 | Biswas | |
| 4,932,962 A | 6/1990 | Yoon et al. | |
| 4,938,760 A | 7/1990 | Burton et al. | |
| 4,969,892 A | 11/1990 | Burton et al. | |
| 5,007,894 A | 4/1991 | Enhorning | |
| 5,012,822 A | 5/1991 | Schwarz | |
| 5,013,292 A | 5/1991 | Lemay | |
| 5,019,032 A | 5/1991 | Robertson | |
| 5,032,508 A | 7/1991 | Naughton et al. | |
| 5,036,867 A | 8/1991 | Biswas | |
| 5,053,043 A | 10/1991 | Gottesman et al. | |
| 5,085,661 A | 2/1992 | Moss | |
| 5,112,344 A | 5/1992 | Petros | |
| 5,123,428 A | 6/1992 | Schwarz | |
| 5,188,636 A | 2/1993 | Fedotov | |
| 5,207,679 A * | 5/1993 | Li | 606/232 |
| 5,209,756 A | 5/1993 | Seedhom et al. | |
| 5,250,033 A | 10/1993 | Evans et al. | |
| 5,256,133 A | 10/1993 | Spitz | |
| 5,281,237 A | 1/1994 | Gimpelson | |
| 5,328,077 A | 7/1994 | Lou | |
| 5,337,736 A | 8/1994 | Reddy | |
| 5,362,294 A | 11/1994 | Seitzinger | |
| 5,368,595 A | 11/1994 | Lewis | |
| 5,383,904 A | 1/1995 | Totakura et al. | |
| 5,386,836 A | 2/1995 | Biswas | |
| 5,403,328 A | 4/1995 | Shellman | |
| 5,413,598 A | 5/1995 | Moreland | |
| 5,439,467 A | 8/1995 | Benderev et al. | 606/139 |
| 5,520,700 A | 5/1996 | Beyar et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,591,163 A | 1/1997 | Thompson | |
| 5,611,515 A | 3/1997 | Benderev et al. | |
| 5,628,756 A | 5/1997 | Barker, Jr. et al. | |
| 5,633,286 A | 5/1997 | Chen | |
| 5,669,935 A | 9/1997 | Rosenman et al. | |
| 5,683,349 A | 11/1997 | Makower et al. | |
| 5,807,403 A | 9/1998 | Beyar et al. | |
| 5,836,314 A | 11/1998 | Benderev et al. | |
| 5,836,315 A | 11/1998 | Benderev et al. | |
| 5,840,011 A | 11/1998 | Landgrebe et al. | 600/30 |
| 5,842,478 A | 12/1998 | Benderev et al. | |
| 5,860,425 A | 1/1999 | Benderev et al. | |
| 5,899,909 A | 5/1999 | Claren et al. | 606/119 |
| 5,919,232 A | 7/1999 | Chaffringeon et al. | |
| 5,934,283 A | 8/1999 | Willem et al. | |
| 5,935,122 A | 8/1999 | Fourkas et al. | |
| 5,944,732 A | 8/1999 | Raulerson et al. | |
| 5,972,000 A | 10/1999 | Beyar et al. | |
| 5,988,171 A | 11/1999 | Sohn et al. | |
| 5,997,554 A | 12/1999 | Thompson | |
| 6,010,447 A | 1/2000 | Kardjian | |
| 6,030,393 A | 2/2000 | Corlew | |
| 6,031,148 A | 2/2000 | Hayes et al. | |
| 6,042,534 A * | 3/2000 | Gellman et al. | 600/30 |
| 6,042,536 A | 3/2000 | Tihon et al. | |
| 6,050,937 A | 4/2000 | Benderev | |
| 6,053,935 A | 4/2000 | Brenneman et al. | |
| 6,068,591 A | 5/2000 | Bruckner et al. | |
| 6,071,290 A | 6/2000 | Compton | |
| 6,106,545 A | 8/2000 | Egan | |
| 6,110,101 A | 8/2000 | Tihon et al. | |
| 6,117,067 A | 9/2000 | Gil-Vernet | |
| 6,168,611 B1 | 1/2001 | Risvi | |
| 6,221,005 B1 | 4/2001 | Bruckner et al. | |
| 6,267,766 B1 * | 7/2001 | Burkhart | 606/232 |
| 6,273,852 B1 | 8/2001 | Lehe et al. | |
| 6,302,840 B1 | 10/2001 | Benderev | |
| 6,306,079 B1 | 10/2001 | Trabucco | |
| 6,328,744 B1 | 12/2001 | Harari et al. | |
| 6,334,446 B1 | 1/2002 | Beyar | |
| 6,352,553 B1 | 3/2002 | van de Burg et al. | |
| 6,382,214 B1 | 5/2002 | Raz et al. | |
| 6,406,423 B1 | 6/2002 | Scetbon | |
| 6,406,480 B1 | 6/2002 | Beyar et al. | |
| 6,475,139 B1 | 11/2002 | Miller | |
| 6,478,727 B2 | 11/2002 | Scetbon | |
| 6,482,214 B1 | 11/2002 | Sidor, Jr. et al. | |
| 6,494,906 B1 | 12/2002 | Owens | |
| 6,502,578 B2 | 1/2003 | Raz et al. | |
| 6,530,943 B1 | 3/2003 | Hoepffner et al. | |
| 6,582,443 B2 | 6/2003 | Cabak et al. | |
| 6,638,284 B1 | 10/2003 | Rousseau et al. | |
| 6,689,047 B2 * | 2/2004 | Gellman | 600/30 |
| 6,695,855 B1 * | 2/2004 | Gaston | 606/151 |
| 2001/0000533 A1 | 4/2001 | Kovac | |
| 2001/0049467 A1 | 12/2001 | Lehe et al. | 600/30 |
| 2002/0022841 A1 | 2/2002 | Kovac | |
| 2002/0028980 A1 | 3/2002 | Thierfelder et al. | |
| 2002/0055748 A1 | 5/2002 | Gellman et al. | |
| 2002/0058959 A1 | 5/2002 | Gellman | |
| 2002/0068948 A1 | 6/2002 | Stormby et al. | |
| 2002/0072694 A1 | 6/2002 | Snitkin et al. | |
| 2002/0077526 A1 | 6/2002 | Kammerer et al. | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0099260 A1 | 7/2002 | Suslian et al. | |
| 2002/0107430 A1 | 8/2002 | Neisz et al. | |
| 2002/0107525 A1 | 8/2002 | Harari et al. | |
| 2002/0115906 A1 | 8/2002 | Miller | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151762 A1 | 10/2002 | Rocheleau et al. | |
| 2002/0151909 A1 | 10/2002 | Gellman et al. | |
| 2002/0151910 A1 | 10/2002 | Gellman et al. | |
| 2002/0156487 A1 | 10/2002 | Gellman et al. | |
| 2002/0156488 A1 | 10/2002 | Gellman et al. | |
| 2002/0188169 A1 | 12/2002 | Kammerer et al. | |
| 2003/0004395 A1 | 1/2003 | Therin | |
| 2003/0004581 A1 | 1/2003 | Rousseau | |
| 2003/0009181 A1 | 1/2003 | Gellman et al. | |
| 2003/0023136 A1 | 1/2003 | Raz | |
| 2003/0023137 A1 | 1/2003 | Gellman | |
| 2003/0023138 A1 | 1/2003 | Luscombe | |
| 2003/0036676 A1 | 2/2003 | Scetbon | |
| 2003/0045774 A1 | 3/2003 | Staskin et al. | |
| 2003/0050530 A1 | 3/2003 | Neisz et al. | |
| 2003/0065246 A1 | 4/2003 | Inman et al. | |
| 2003/0065402 A1 | 4/2003 | Anderson et al. | |
| 2003/0114866 A1 | 6/2003 | Ulmsten et al. | |
| 2003/0176762 A1 | 9/2003 | Kammerer | |

FOREIGN PATENT DOCUMENTS

| | | |
|---|---|---|
| EP | 0 470 308 A1 | 2/1992 |
| EP | 0 650 703 A1 | 6/1994 |
| EP | 0 643 945 A2 | 7/1994 |
| EP | 1 093 758 A1 | 4/2001 |
| EP | 1 060 714 A3 | 9/2002 |
| IT | 1299162 | 4/1998 |
| WO | WO 93/17635 A1 | 9/1993 |
| WO | WO 93/19678 A2 | 10/1993 |
| WO | WO 97/16121 | 5/1997 |
| WO | WO 98/19606 A1 | 5/1998 |
| WO | WO 98/35616 A1 | 8/1998 |

(56) References Cited

FOREIGN PATENT DOCUMENTS

| | | |
|---|---|---|
| WO | WO 98/35632 A1 | 8/1998 |
| WO | WO 99/16381 A1 | 4/1999 |
| WO | WO 99/52450 A1 | 10/1999 |
| WO | WO 00/64370 A1 | 2/2000 |
| WO | WO 00/13601 A1 | 3/2000 |
| WO | WO 00/18319 A1 | 4/2000 |
| WO | WO 00/27304 A1 | 5/2000 |
| WO | WO 00/57812 A1 | 10/2000 |
| WO | WO 00/74594 A1 | 12/2000 |
| WO | WO 00/74613 A1 | 12/2000 |
| WO | WO 00/74633 A2 | 12/2000 |
| WO | WO 01/06951 A1 | 2/2001 |
| WO | WO 01/26581 A1 | 4/2001 |
| WO | WO 01/39670 A1 | 6/2001 |
| WO | WO 01/45589 | 6/2001 |
| WO | WO 01/56499 A1 | 8/2001 |
| WO | WO 02/28312 A1 | 4/2002 |
| WO | WO 02/32284 A2 | 4/2002 |
| WO | WO 02/34124 A2 | 5/2002 |
| WO | WO 02/38079 A2 | 5/2002 |
| WO | WO 02/39890 A2 | 5/2002 |
| WO | WO 02/071953 A2 | 9/2002 |
| WO | WO 02/078552 A1 | 10/2002 |
| WO | WO 03/017848 A1 | 3/2003 |
| WO | WO 03/026585 A2 | 4/2003 |
| WO | WO 03/037215 A2 | 5/2003 |
| WO | WO 03/041613 A1 | 5/2003 |
| WO | WO 03/047435 A1 | 6/2003 |

OTHER PUBLICATIONS

Araki, Tohru et al., The Loop-Loosening Procedure for Urination Difficulties After Stamey Suspension of the Vesical Neck, The Journal of Urology, vol. 144, pp. 319-323 (Aug. 1990).

Asmussen, M. et.al., Simultaneous Urethro-Cystometry With a New Technique, Scand J Urol Nephrol 10, p. 7-11 (1976).

Beck, Peter R. et al., Treatment of Urinary Stress Incontinence With Anterior Colporrhaphy, Obstetrics and Gynecology, vol. 59 (No. 3), pp. 269-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40. No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).

Blaivas, Jerry et al., Pubovaginal Fascial Sling for the Treatment of Complicated Stress Urinary Incontinence, The Journal of Urology, vol. 145 (6), pp. 1214-1218 (Jun. 1991).

Blaivas, Jerry, et al., Type III Stress Urinary Incontinence: Importance of Proper Diagnosis and Treatment, Surgical Forum, pp. 473-475, (1984).

Blavis, Jerry, Commentary: Pubovaginal Sling Procedure, Experience with Pubovaginal Slings, pp. 93-101 (1990).

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Choe, Jong M. et al., GORE-TEX Patch Sling: 7 Years Later, Urology, vol. 54, pp. 641-646 (1999).

Cook/Ob Gyn®, Urogynecology, Copyright Cook Urological Inc., pp. 1-36 (1996).

Das, Sakti et al., Laparoscopic Colpo-Suspension, The Journal of Urology, vol. 154, pp. 1119-1121 (Sep. 1995).

Decter, Ross M., Use of the Fascial Sling for Neurogenic Incontinence: Lessons Learned, The Journal of Urology, vol. 150, pp. 683-686 (Aug. 1993).

DeLancey, John, MD, Structural Support of the Urethra as It Relates to Stress Urinary Incontinence: The Hammock Hypothesis, Am J Obstet Gynecol, vol. 170 No. 6, pp. 1713-1723 (Jun. 1994).

Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69, pp. 45-50 (1990).

Falconer, C. et al., Clinical Outcome and Changes in Connective Tissue Metabolism After Intravaginal Slingplasty in Stress Incontinence Women, International Urogynecology Journal, pp. 133-137 (1966).

Falconer, C. et al., Influence of Different Sling Materials of Connective Tissue Metabolism in Stress Urinary Incontinent Women, International Urogynecology Journal, Supp. 2, pp. S19-S23 (2001).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology, vol. 138 (Sep. 1987).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).

Hodgkinson, C. Paul et.al., Urinary Stress Incontinence in the Female, Department of Gynecology and Obstetrics, Henry Ford Hospital, vol. 10, No. 5, p. 493-499, (Nov. 1957).

Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).

Ingelman-Sunberg, A. et al., Surgical Treatment of Female Urinary Stress Incontinence, Contr. Gynec. Obstet., vol. 10, pp. 51-69 (1983).

Jeffcoate, T.N.A. et al., The Results of the Aldridge Sling Operation for Stress Incontinence, Journal of Obstetrics and Gynaecology, pp. 36-39 (1956).

Karram, Mickey et al., Patch Procedure: Modified Transvaginal Fascia Lata Sling for Recurrent for Severe Stress Urinary Incontinence, vol. 75, pp. 461-463 (Mar. 1990).

Kersey, J., The Gauze Hammock Sling Operation in the Treatment of Stress Incontinence, British Journal of Obstetrics and Gynaecology, vol. 90, pp. 945-949 (Oct. 1983).

Klutke, Carl et al., The Anatomy of Stress Incontinence: Magentic Resonance Imaging of the Female Bladder Neck and Urethra, The Journal of Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Klutke, John M.D. et al, The promise of tension-free vaginal tape for female SUI, Contemporary Urology, 7 pages (Oct. 2000).

Korda, A. et al., Experience With Silastic Slings for Female Urinary Incontinence, Aust NZ J. Obstet Gynaecol, vol. 29, pp. 150-154 (May 1989).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Kovac, Stephen Robert, M.D., Cirriculum Vitae, pp. 1-33 (Jun. 18, 1999).

Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).

(56) References Cited

OTHER PUBLICATIONS

Leach, Gary E., MD, Bone Fixation Technique for Transvaginal Needle Suspension, Urology vol. XXXI, No. 5, pp. 388-390 (May 1988).
Lichtenstein, Irving L. et al, The Tension Free Hernioplasty, The American Journal of Surgery, vol. 157 pp. 188-193 (Feb. 1989).
Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).
Marshall, Victor Fray et al. The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at the University of Michigan, Journal of Urology, vol. 138, pp. 90-93(1987).
McGuire, Edwared J. et al., Abdominal Fascial Slings, Slings, Raz Female Urology, p. 369-375 (1996).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739, (Nov. 1966).
Moir, J. Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, For the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Narik, G. et.al., A Simplified Sling Operation Suitable for Routine Use, Gynecological and Obstetrical Clinic, University of Vienna, vol. 84, No. 3, p. 400-405, (Aug. 1, 1962).
Nichols, David H., The Mersilene Mesh Gauze-Hammock for Severe Urinary Stress Incontinence, Obstetrics and Gynecology, vol. 41, pp. 88-93 (Jan. 1973).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Parra, R. O., et al, Experience with a Simplified Technique for the Treatment of Female Stress Urinary Incontinence, British Journal of Urology, vol. 66, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45-50 (1999).
Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69, Sup 153, p. 75 (1990).
Peter Petros et al., Anchoring the Midurethra Restores Bladder-Neck Anatomy and Continence, The Lancet, vol. 354, pp. 997-998 (Sep. 18, 1999).
Petros, Peter E. Papa, et al., An Anatomical Basis for Success and Failure of Female Incontinence Surgery, Scandinavian Journal of Neurourology and Urodynamics, Sup 153, pp. 55-60 (1993).
Petros, Peter E. Papa, et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Therory of Female Urinary Incontinence, Acta Obstetricia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa, et al., Cough Transmission Ratio: An Indicator of Suburethral Vaginal Wall Tension Rather Than Urethral Closure?, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "TUCK"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Applications of the Theory—Development of the Intravaginal Sling PKLASTY (IVS) Procedure, Scandinavian Journal of Neurourology and Urodynamics, Sup 153, pp. 53-54 (1993).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand vol. 69, Sup 153, pp. 53-59 (1990).
Petros, Peter E. Papa et al., The Development of the Intravaginal Slingplasty Procedure: IVS II—(With Bilateral "TUCKS"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Schandinavian Journal of Neurology and Urodynamics, Sup 153, pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurology and Urodynamics, Sup 153, p. 73-75 (1993).

(56) References Cited

OTHER PUBLICATIONS

Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).

Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).

Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).

Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).

Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).

Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).

Petros, Peter E. Papa, Development of Generic Models for Ambulatory Vaginal Surgery—Preliminary Report, International Urogynecology Journal, pp. 20-27 (1998).

Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dysfunction, vol. 8 (5), pp. 270-278, (1997).

Rackley, Raymond R. et al., Tension-Free Vaginal Tape and Percutaneous Vaginal Tape Sling Procedures, Techniques in Urology, vol. 7, No. 2, pp. 90-100 (2001).

Rackley, Raymond R. M.D., Synthetic Slings: Five Steps for Successful Placement, Urology Times, p. 46,48,49 (Jun. 2000).

Raz, Shlomo, et al., The Raz Bladder Neck Suspension Results in 206 Patients, The Journal of Urology, pp. 845-846 (1992).

Raz, Shlomo, Female Urology, pp. 80-86, 369-398, 435-442 (1996).

Raz, Shlomo, MD, Modified Bladder Neck Suspension for Female Stress Incontinence, Urology vol. XVII, No. 1, pp. 82-85 (Jan. 1981).

Richardson, David A. et al., Delayed Reaction to the Dacron Buttress Used in Urethropexy, The Journal of Reproductive Medicine, pp. 689-692, vol. 29, No. 9 (Sep. 1984).

Ridley, John H., Appraisal of the Goebell-Frangenheim-Stoeckel Sling Procedure, American Journal Obst. & Gynec., vol. 95, No. 5, pp. 714-721 (Jul. 1, 1986).

Roberts, Henry, M.D., Cystourethrography in Women, Deptment of Obstetrics and Gynaecology, University of Liverpool, May 1952, vol. XXXV, No. 293, pp. 253-259.

Sloan, W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).

Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).

Stamey, Thomas A., M.D., Endoscopic Suspension of the Vesical Neck for Urinary Incontinence in Females, Ann. Surgery, vol. 192 No. 4, pp. 465-471 (Oct. 1980).

Stanton, Stuart L., Suprapubic Approaches for Stress Incontinence in Women, Journal of American Geriatics Society, vol. 38, No. 3, pp. 348-351 (Mar. 1990).

Stanton, Stuart, Springer-Veglag, Surgery of Female Incontinence, pp. 105-113 (1986).

Staskin, David R., et al., The Gore-Tex Sling Procedure for Female Sphincteric Incontinence: Indications, Technique, and Results, World Journal of Urology, vol. 15, pp. 295-299 (1997).

Studdiford, William E., Transplantation of Abdominal Fascia for the Relief of Urinary Stress Incontinence, American Journal of Obstetrics and Gynecology pp. 764-775 (1944).

TVT Tension-free Vaginal Tape, Gynecare, Ethicon, Inc., 23 pages (1999).

Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).

Ulmsten, U. et al., An Ambulatory Surgical Procedure Under Local Anesthesia for Treatment of Female Urinary Incontinence, International Urogynecology Journal, vol. 7, pp. 81-86, (1996).

Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Ulmsten, Ulf et al., Different Biochemical Composition of Connective Tissue in Continent, Acta Obstet Gynecol Scand, pp. 455-457 (1987).

Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).

Ulmsten, Ulf et al., The Unstable Female Urethra, Am. J. Obstet. Gynecol., vol. 144 No. 1, pp. 93-97 (Sep. 1, 1982).

Vesica® Percutaneous Bladder Neck Stabilization Kit, a New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Webster, George et al., Voiding Dysfunction Following Cystourethropexy: Its Evaluation and Management, The Journal of Urology, vol. 144, pp. 670-673 (Sep. 1990).

Winter, Chester C., Peripubic Urethropexy for Urinary Stress Incontinence in Women, Urology, vol. XX, No. 4, pp. 408-411 (Oct. 1982).

Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert et al., Pulsion Enterocele: Long-Term Results of an Abdominoperineal Technique, Obstetrics & Gynecology, vol. 55 No. 2, pp. 141-148 (Feb. 1980).

Zacharin, Robert, The Suspensory Mechanism of the Female Urethra, Journal of Anatomy, vol. 97, Part 3, pp. 423-427 (1963).

Zimmern, Phillippe E. et al., Four-Corner Bladder Neck Suspension, Vaginal Surgery for the Urologist, vol. 2, No. 1, pp. 29-36 (Apr. 1994).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Boyles, Sarah Hamilton et al., Procedures for Urinary Incontinence in the United States, 1979-1997, Am J Obstet Gynecol, vol. 189, n. 1, pp. 70-75 (Jul. 2003).

Cervigni, Mauro et al., The Use of Synthetics in the Treatment of Pelvic Organ Prolapse, Voiding Dysfunction and Female Urology, vol. 11, pp. 429-435 (2001).

Dargent, D. et al., Insertion of a Suburethral Sling Through the Obturator Membrane in the Treatment of Female Urinary Incontinence, Gynecol Obstet Fertil, vol. 30, pp. 576-582 (2002).

(56) References Cited

OTHER PUBLICATIONS

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
U.S. Appl. No. 60/356,697, Feb. 14, 2002, Kammerer.
Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).
Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).
Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).
Flood, C.G. et al., Anterior Colporrhaphy Reinforce With Marlex Mesh for the Treatment of Cystoceles, International Urogynecology Journal, vol. 9, pp. 200-204 (1998).
Guner, et al., Transvaginal Sacrospinous Colpopexy for Marked Uterovaginal and Vault Prolapse, Inter J of Gynec & Obstetrics, vol. 74, pp. 165-170 (2001).
Heit, Michael et al., Predicting Treatment Choice for Patients With Pelvic Organ Prolapse, Obstetrics & Gynecology, vol. 101, n. 6, pp. 1279-1284 (Jun. 2003).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'Un Treillis Synthetique Dans La Cure Par Voie Vaginale Des Prolapsus Genitaux, J Gynecol Obstet Biol Reprod, vol. 28, pp. 825-829 (1999).
Marchionni, Mauro et al., True Incidence of Vaginal Vault Prolapse—Thirteen Years of Experience, Journal of Reproductive Medicine, vol. 44, n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Migliari, Roberto et al., Tension-Free Vaginal Mesh Repair for Anterior Vaginal Wall Prolapse, Eur Urol, vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Morley, George W. et al., Sacrospinous Ligament Fixations for Eversion of the Vagina, Am J Obstet Gyn, vol. 158, n. 4, pp. 872-881 (Apr. 1988).
Natale, F. et al., Tension Free Cystocele Repair (TCR): Long-Term Follow-Up, International Urogynecology Journal, vol. 11, supp. 1, p. S51 (Oct. 2000).
Nicita, Giulio, A New Operation for Genitourinary Prolapse, Journal of Urology, vol. 160, pp. 741-745 (Sep. 1998).
Niknejad, Kathleen et al., Autologous and Synthetic Urethral Slings for Female Incontinence, Urol Clin N Am. vol. 29, pp. 597-611 (2002).
Paraiso et al., Laparoscopic Surgery for Enterocele, Vaginal Apex Prolapse and Rectocele, Int. Urogynecol J, vol. 10, pp. 223-229 (1999).
Petros, Peter E. Papa et al., The Intravaginal Slingplasty Operation, a Minimally Invasive Technique for Cure of Urinary Incontinence in the Female, Aust. NZ J Obstet Gynaecol, vol. 36, n. 4, pp. 453-461 (1996).
Petros, Peter E. Papa, Vault Prolapse II; Restoration of Dynamic Vaginal Supports by Infracoccygeal Sacropexy, an Axial Day-Case Vaginal Procedure, Int Urogynecol J, vol. 12, pp. 296-303 (2001).
Richter, K., Massive Eversion of the Vagina: Pathogenesis, Diagnosis and Therapy of the "True" Prolapse of the Vaginal Stump, Clin obstet gynecol, vol. 25, pp. 897-912 (1982).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Swift, S.E., et al., Case-Control Study of Etiologic Factors in the Development of Sever Pelvic Organ Prolapse, Int Urogynecol J, vol. 12, pp. 187-192 (2001).
Villet, R., Reponse De R. Villet A L'Article De D. Dargent et al., Gynécolgie Obstétrique & Fertilité, vol. 31, p. 96 (2003).
Weber, Anne M. et al., Anterior Vaginal Prolapse: Review of Anatomy and Techniques of Surgical Repair, Obstetrics and Gynecology. vol. 89, n. 2, pp. 311-318 (Feb. 1997).
Winters et al., Abdominal Sacral Colpopexy and Abdominal Enterocele Repair in the Management of Vaginal Vault Prolapse, Urology, vol. 56, supp. 6A, pp. 55-63 (2000).
"We're staying ahead of the curve" Introducing the IVS Tunneller Device for Tension Free Procedures, Tyco Healthcare, 3 pages (2002).
Advantage A/T™, Surgical Mesh Sling Kit, Boston Scientific, 6 pages (2002).
Capio™ CL—Transvaginal Suture Capturing Device—Transvaginal Suture Fixation to Cooper's Ligament for Sling Procedures, Boston Scientific, Microvasive®, 8 pages, (2002).
Gynecare TVT Tension-Free Support for Incontinence, The tension-free solution to female Incontinence, Gynecare Worldwide, 6 pages, (2002).
IVS Tunneller—A UNIVERSAL instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
McGuire™ Suture Buide, The McGuire™ Suture Guide, a single use instrument designed for the placement of a suburethral sling, Bard, 2 pages (2001).
Sabre™ Bioabsorbable Sling, Generation Now, Mentor, 4 pages (May 2002).
Sabre™ Surgical Procedure, Mentor, 6 pages (Aug. 2002).

\* cited by examiner

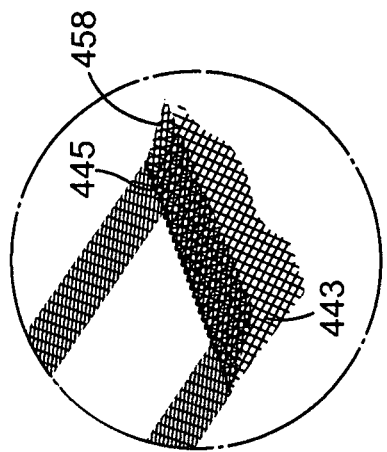
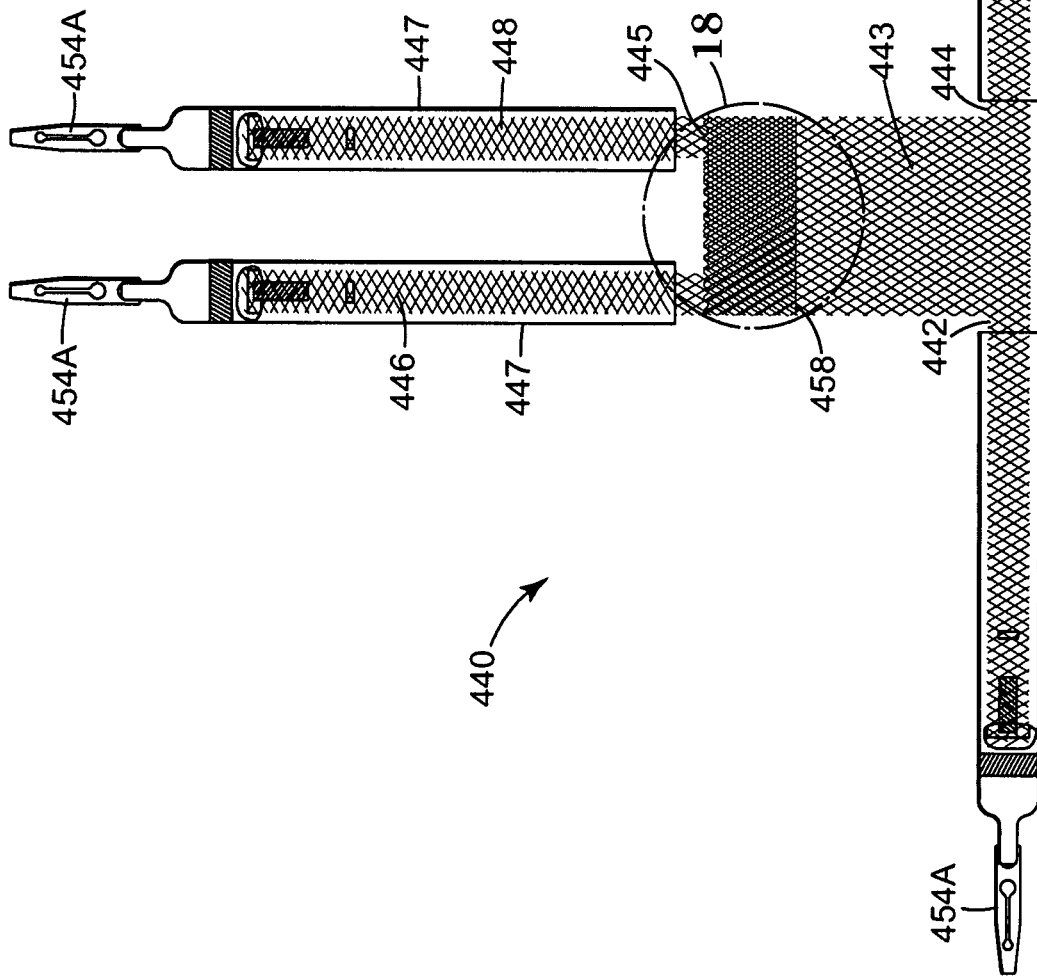

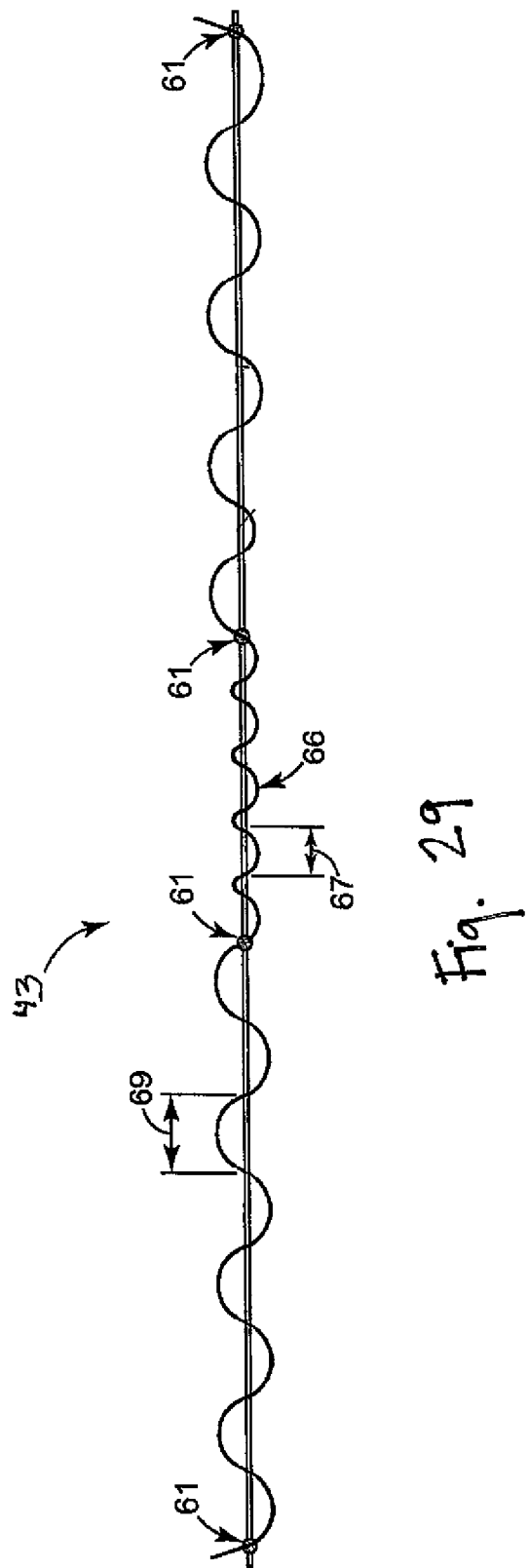

PELVIC HEALTH IMPLANTS AND METHODS

CROSS REFERENCE TO RELATED APPLICATIONS

The present application is a continuation of Ser. No. 10/423,662, filed Apr. 25, 2003 now U.S. Pat. No. 7,407,480, which is a continuation-in-part of U.S. patent application Ser. No. 09/917,443, filed Jul. 27, 2001 now U.S. Pat. No. 6,612,977 and of U.S. patent application Ser. No. 10/280,341, filed Oct. 25, 2002 now U.S. Pat. No. 6,971,986, and claims priority to both utility applications and to U.S. Provisional Application Ser. No. 60/380,591, filed May 15, 2002; and U.S. Provisional Application Ser. No. 60/456,750, filed Mar. 21, 2003. The entire contents of all of those patent applications are herein incorporated by reference.

BACKGROUND

Pelvic floor disorders include cystocele, rectocele, enterocele, and prolapse such as anal, uterine and vaginal vault prolapse. A cystocele is a hernia of the bladder, usually into the vagina and introitus. These disorders typically result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Synthetic implants have been used to address pelvic organ prolapse. See Julian, *The Efficacy of Marlex Mesh in the Repair of Severe, Recurrent Vaginal Prolapse of the Anterior Midvaginal Wall*, Am. J. Obstet Gynec, Vol. 175, No. 6 (1996) (Pps 1472-1475). A hammock-shaped polypropylene mesh is described in Nicita, *A New Operation For Genitourinary Prolapse*, J. of Urology, Vol. 160, 741-745 (September 1998). The mesh is taut and anchored transversely between the two arcus tendineus of the endopelvic fascia and in the anteroposterior direction between the bladder and uterine necks. The width of the mesh is equal to the anteroposterior dimension of cystocele.

Migliari et al used a 5×5 cm mixed (60% polyglactin 910 and 40% polyester) fiber mesh to treat cystocele. See Migliari et al., *Treatment Results Using a Mixed Fiber Mesh in Patients With Grade IV Cystocele*, J. of Urology, Vol. 161, 1255-1258 (April 1998). Meshes provided in square or rectangular configurations must be trimmed to form a complex shape. This can add to the length of the surgical procedure.

Vaginal vault prolapse is often associated with a rectocele, cystocele or enterocele. It is known to repair vaginal vault prolapse by suturing to the utero sacral ligaments, the sacrospinous ligaments or the levator muscles. It is also known to repair prolapse by attaching the vaginal vault through mesh or fascia to the sacrum. Many patients suffering from vaginal vault prolapse also require a surgical procedure to correct stress urinary incontinence that is either symptomatic or latent.

Italian Patent No. 01299162 describes a first prosthesis mesh having a first section designed to be applied to a bladder cavity and a second section designed to be applied to the bladder below the bladder neck. The first prosthesis includes a pair of flaps that are designed to be applied to the urethropelvic ligament and are separated from the first section by slits. The first prosthesis may be used to treat urogenital prolapse. A second prosthesis for treating rectocele is disclosed. The second prosthesis is separate and distinct from the first prosthesis.

A sacral colpopexy is a procedure for providing vaginal vault suspension. It may be performed through an abdominal incision or laparoscopically. Complications include mesh infection, mesh erosion, bowel obstruction, and bleeding from the presacral venous complex. Typically, this procedure is accompanied by an abdominal enterocele repair and cul-de-sac obliteration.

A sacral colpopexy entails suspension of the vaginal cuff to the sacrum with fascia or synthetic mesh. The synthetic mesh is typically carefully customized or assembled into a special shape by the surgeon. A surgeon manually cuts a sheet of the mesh and stitches elements of the mesh to form the special shape. The literature reports surgeons suturing mesh material into various T-shaped articles. See Paraiso et al, *Laparoscopic Surgery for Enterocele, Vaginal Apex Prolapse and Rectocele*, Int Urogynecol J (1999), 10:223-229.

A sacral colpopexy can be a tedious, challenging surgical procedure. Average procedure lengths of 247 minutes were reported in Winters et al., *Abdominal Sacral Colpopexy and Abdominal Enterocele Repair in the Management of Vaginal Vault Prolapse*, Urology 56 (Suppl 6A) (2000): 55-63. At least some of this time can be attributed to the time required for the surgeon to construct an implant. Non-laparoscopic surgical procedure lengths can be shorter, but such procedures involve a large abdominal incision with the attendant risk of morbidity and infection. Many surgeons seek to avoid sacral colpopexy procedures for a variety of different reasons, including the amount of surgical activity in proximity to sensitive areas such as the sacrum.

It is reported that 72% of patients with vault prolapse had a combination of other pelvic floor defects. See Richter K. *Massive Eversion of the Vagina: Pathogenesis, Diagnosis and Therapy of the True Prolapse of the Vaginal Stump*, Clin. Obstet Gynecol 25:897-912 (1982). If surgical correction of cystocele, rectocele or stress incontinence is performed in the presence of untreated vaginal vault prolapse, it is speculated that an early recurrence of prolapse is extremely likely. When it is considered that it is often necessary to correct multiple pelvic floor disorders simultaneously, the time factor for surgeons is particularly challenging. See, Diana et al., *Treatment of Vaginal Vault Prolapse with Abdominal Sacral Colpopexy Using Prolene Mesh*, American Journal of Surgery, Vol. 179, (February 2000), Pps. 126-128.

A sacrospinous ligament fixation surgical procedure is a procedure that involves attaching the vault of the vagina to the sacrospinous ligament. See Guner et al., *Transvaginal Sacrospinous Colpopexy For Marked Uterovaginal and Vault Prolapse*, Inter. J. of Gynec. & Obstetrics, 74 (2001) Pps. 165-170. Sacrospinous ligament fixation procedures are believed to require specialized, technical skills. There are additional drawbacks. For example, the procedure tends to place the vagina in an artificial anatomical position (as opposed to a natural position), especially if the procedure is performed unilaterally which tends to pull the vagina to one side.

U.S. Pat. No. 5,840,011 discloses an implant for suspension of the urinary bladder to treat incontinence. The implant includes four securement appendages. The patent states that two securement appendages are drawn retrosymphyseally between the bladder and vagina and are positioned exactly. The other two securement appendages are fixed to the ligamentum pubicum superior behind the two pubic rami.

U.S. Pat. No. 6,306,079 discloses a mesh pubovaginal sling comprising two mesh pieces, including a first mesh portion of polypropylene and a second mesh portion comprising an absorbable material. One piece is inserted at the endopelvic fascia and the other at the suprapubic region.

PCT Publication No. WO 00/64370 (Gaston) describes a device for treating a prolapse by vaginal suspension. The device comprises an elongate, flexible, pierced material, a suture connected to the material and a suture needle joined to the suture. The device is long enough to enable posterior suspension of the vagina at the promontory (i.e. the front upper part of the sacrum). The other end of the device includes a distal portion having a width such that it can cover at least a large part of the posterior part of the vagina, a rounded cut-out with dimensions that enable it to be engaged around the base of the vagina on at least a large part of the lower half of the wall of the vagina. The suture is connected to the article so that it is offset sidewise in relation to the cut-out.

PCT Publication No. WO 00/27304 (ORY et al.) discloses a suspension device for treating prolapse and urinary incontinence. The device comprises at least one filiform suspension cord with limited elasticity and at least two anchoring parts linked to the ends of the cord.

U.S. Pat. No. 5,112,344 and PCT Publication No. PCT/US02/32284 disclose surgical devices for female pelvic health procedures. The IVS Tunneller device is available from U.S. Surgical of Norwalk, Conn. The IVS device comprises a fixed delta wing handle, a hollow metal tube and a stylet that is placeable within the tube. The stylet has a rounded plastic tip on one end and an eyelet at the other end. The device may be used to implant a polypropylene tape for infracoccygeal sacropexy and other surgical procedures. See Farnsworth, *Posterior Intravaginal Slingplasty (Infracoccygeal Sacropexy) For Severe Posthysterectomy Vaginal Vault Prolapse—A Preliminary Report on Safety and Efficacy*, Int. Urogynecol. J. (2002) 13:4-8; Petros, *Vault Prolapse II. Restoration of Dynamic Vaginal Supports by Infracoccygeal Sacropexy, an Axial Day-Case Vaginal Procedure*, Int Urogynecol J (2001) 12:296-303; and Petros, *The Intravaginal Slingplasty Operation, a Minimally Invasive Technique for Cure of Urinary Incontinence in the Female*, Aust. NZ J Obstet Gynaecol, (1996); 36: 4:453.

A single, rigid, hollow metal tube is associated with the IVS Tunneller device. This single tube passes through two separate regions of the patient's body with the attendant risk of cross contamination. The outer diameter of the tube is also relatively large (about 0.25 inches) with the attendant risk of tissue damage due to a large diameter needle.

The polypropylene tape supplied with the IVS Tunneller is a thin, rectangular shape, believed to be approximately 8 mm×350 mm. The thin, rectangular tape supplied with the IVS Tunneller is not believed to be optimally sized and shaped to afford concomitant procedures such as enterocoele, cystocele and/or rectocoele repairs encountered in many cases. The tape is also inextensible. Under a longitudinal force, the implant is highly resistant to elongation. It is believed that inextensible polypropylene tapes may be apt to exhibit a greater association with erosion and failure.

SUMMARY OF THE INVENTION

In one aspect, the present invention comprises a novel implant suitable for addressing one or more disorders including incontinence, cystocoele, rectocoele, enterocoele and prolapse (e.g. uterine and/or vaginal vault). Preferably, the implant is conformable to irregular surfaces and to accommodate different anatomy shapes and sizes. In one embodiment, the implant is preassembled or pre-cut in a predetermined shape to simultaneously address incontinence and cystocele repairs in a tension-free manner and to afford efficient use of the surgeon's time. In another embodiment, the implant includes features affording convenient assembly of a composite implant so that the implant may be customized according to the surgeon's preference or the needs of a particular surgical procedure. In yet another embodiment, the implant includes indicia for convenient trimming of a bulk implant to address the particular needs of a procedure.

In one aspect, the present invention comprises a mesh having a major portion that is sized and shaped to afford repair of a cystocele. The implant is preferably secured in the body without lifting the patient's bladder and without placing tension on the bladder. The implant includes a urethral support portion capable of being placed underneath the patient's urethra; and first and second sling appendages to be placed on different sides of the urethra.

The sling appendages may be sized and shaped to be secured in the patient's abdominal rectus fascia. Alternatively, the sling appendages may be sized and shaped to extend from a region near the patient's urethra to at least the patient's obturator foramen.

The portion of the implant generally opposite the sling appendages may take a variety of different forms. In one embodiment, the portion of the implant opposite the sling appendages may be designed to merely address a cystocele or both a cystocele and a rectocele. In another embodiment, it may be sufficiently long and appropriately shaped to extend to incisions on opposite sides of the patient's anus. In another embodiment, it may have a length sufficient to afford anchoring in the region of the patient's sacrum, or the sacrospinous ligaments, or the uterosacral ligaments, or the levator ani tissues.

For certain configurations of implant and for certain uses of the implant (e.g. posterior vaginal vault repair), the present invention comprises constructing the implant from a longitudinally extendable material. This affords an implant that is relatively longitudinally extendable, unlike prior art implants used in posterior vault repair procedures. In this aspect, the present invention comprises a synthetic mesh material having a portion adapted to be secured in the patient's vaginal region, a first posterior securement appendage that is sized, shaped and configured to extend from the patient's vaginal region to a first incision in the patient's buttocks that is lateral to the patient's anus; and a second posterior securement appendage that extends to the opposite side of the patient's anus.

The bulk material from which the mesh is supplied has at least a Longitudinal Elongation Factor (LEF) of at least 0.06 under a ½ pound load. More preferably, the bulk material from which the mesh is supplied has at least a Longitudinal Elongation Factor (LEF) of more than about 0.08 under a ½ pound load, even more preferably it is more than about 0.15. Preferably, bulk material from which the mesh is supplied has a Longitudinal Elongation Factor (LEF) of more than about 0.08 under a 1 pound load, more preferably it is more than about 0.1 under a 1 pound load, and even more preferably it is more than about 0.2 under a 1 pound load.

Preferably, the synthetic mesh materials used comprise bulk knitted polypropylene monofilaments, but a variety of different materials are contemplated. The implant is preferably knitted to be supple, conformable and to afford tissue ingrowth. In one embodiment the implant is a composite constructed of two different implantable materials.

In another aspect, the present invention comprises a synthetic mesh material having a portion adapted to be secured in the patient's vaginal region, a first posterior securement appendage that is sized, shaped and configured to extend from the patient's vaginal region toward a first incision in the patient's buttocks that is lateral to the patient's anus; a second posterior securement appendage placeable on a side of the patient's anus different than that of the first posterior securement appendage. The implant includes a first flexible insertion sheath associated with at least a portion of the first posterior securement appendage, and a second flexible insertion sheath associated with at least a portion of the second posterior securement appendage.

Preferably, the first and second posterior securement appendages have distal end regions adapted to be secured in the patient's ischioanal or ischiorectal fossa. Alternatively, the first and second posterior securement appendages have distal end regions adapted to be secured in the patient's sacrospinous ligaments or the uterosacral ligaments or levator ani tissue.

In another aspect, the present invention comprises an implant assembly suitable for placement through incisions in the patient's buttocks on opposite sides of the anus. The novel implant assemblies include one or more of: i) connectors for associating the implant assembly with the distal end of an insertion needle, ii) dilators for dilating tissue, iii) insertion sheaths, iv) tensioning sutures, and v) an elongatable, conformable mesh.

In another aspect, the present invention comprises a surgical implant for addressing incontinence and cystocele disorders comprising a synthetic mesh material having a cystocele repair portion adapted to be secured in the patient's vaginal region, a first posterior securement appendage that is sized, shaped and configured to extend from the patient's vaginal region toward a first incision in the patient's buttocks; and a second posterior securement appendage opposite the first. The implant includes a urethral support portion capable of being placed underneath the patient's urethra; a first sling appendage for securement on a first side of the patient's urethra; and a second sling appendage for securement on a side of the patient's urethra generally opposite the first.

In another aspect, the present invention comprises a synthetic mesh material having a portion adapted to be secured in the patient's vaginal region. The mesh has a first posterior securement appendage that is sized, shaped and configured to extend from the patient's vaginal region toward a first incision in the patient's buttocks; and a second posterior securement appendage opposite the first. In this embodiment, the first and second posterior securement appendages include a connector for associating the first and second posterior securement appendages with a distal end of an insertion needle.

The present invention includes surgical kits comprising first and second insertion needles having distal ends. Preferably, the first and second insertion needles are configured so that their distal ends may be initially inserted through an incision in the patient's buttocks and then passed through tissue, emerging through a vaginal incision. The kits also include an implant comprising a synthetic mesh material having a portion adapted to be secured in the patient's vaginal region to repair, for example, a vaginal vault prolapse. The mesh has a first posterior securement appendage that is sized, shaped and configured to extend from the patient's vaginal region toward a first incision in the patient's buttocks; and a second posterior securement appendage generally opposite the first. Preferably, this embodiment includes first and second flexible insertion sheaths associated with at least a portion of the first and second posterior securement appendages.

In another embodiment, the present invention comprises a synthetic mesh having a major portion, and at least four projections extending from the major portion. One of the projections is adapted to be placed on a first side of the patient's urethra and extend from the patient's urethral region to the patient abdominal rectus fascia, and another of the projections is adapted to be placed on a side of the patient's urethra generally opposite the first side. This embodiment preferably includes at least one connector (preferably four) for associating the implant with at least one (preferable four) insertion needle.

In another aspect, the present invention comprises a modular assembly for affording construction of a surgical implant for addressing one or more pelvic floor disorders. The assembly comprises an anterior element for affording a sling-like implant; a posterior element for securement in a posterior region of the patient's body; and a cystocele repair portion for affording repair of a cystocele, wherein the cystocele repair portion may be associated with either the anterior element or the posterior element or both elements. Preferably the assembly includes a means for facilitating association between elements of the assembly. Also preferably, the cystocele repair portion includes indicia to facilitate trimming to adjust the implant to different sizes. A rectocele repair portion may also be provided.

In yet another aspect, the present invention comprises novel surgical procedures that utilize the novel implants and implant assemblies.

BRIEF DESCRIPTION OF THE DRAWINGS

Other features and advantages of the present invention will be seen as the following description of particular embodiments progresses in conjunction with the drawings, in which:

FIGS. 8 through 13 sequentially illustrate an embodiment of a surgical procedure according to an aspect of the present invention, wherein:

FIG. 8 is a schematic view showing the locations of incisions proximate ischioanal fossa or ischiorectal fossa, and two separate needles for passage through an incision;

FIG. 9 schematically illustrates a surgeon passing a surgical needle from the incision proximate the patient's ischioanal fossa or ischiorectal fossa to a vaginal incision;

FIG. 10 is a schematic side view showing the distal end of the needle of FIG. 9 after it emerges from an incision in the region of the vaginal apex, and a dilator connector of an implant;

FIG. 11 is a schematic illustration of the surgeon guiding the distal end of the needle of FIG. 10;

FIG. 12 is a perspective view of an implant after it has been placed in a patient and showing portions of the implant emerging from the incisions proximate the patients ischioanal fossa or ischiorectal fossa;

FIG. 13 is a schematic side view showing one embodiment of implant according to the present invention after it has been inserted in the patient;

FIG. 17 is a bottom view of another embodiment of implant according to the present invention;

FIG. 18 is an enlarged perspective view of a portion of the implant of FIG. 17;

FIG. 28b is a bottom view of the anchor of FIG. 28a.

FIG. 29 is a side view of a sling according to one aspect of the present invention.

DETAILED DESCRIPTION

The following description is meant to be illustrative only and not limiting. Other embodiments of this invention will be apparent to those of ordinary skill in the art in view of this description.

The present invention is directed to surgical instruments, assemblies and implantable articles for treating one or more pelvic floor disorders including cystocele, rectocele, enterocele, incontinence and uterine, anal or vaginal vault prolapse.

Figure 1:
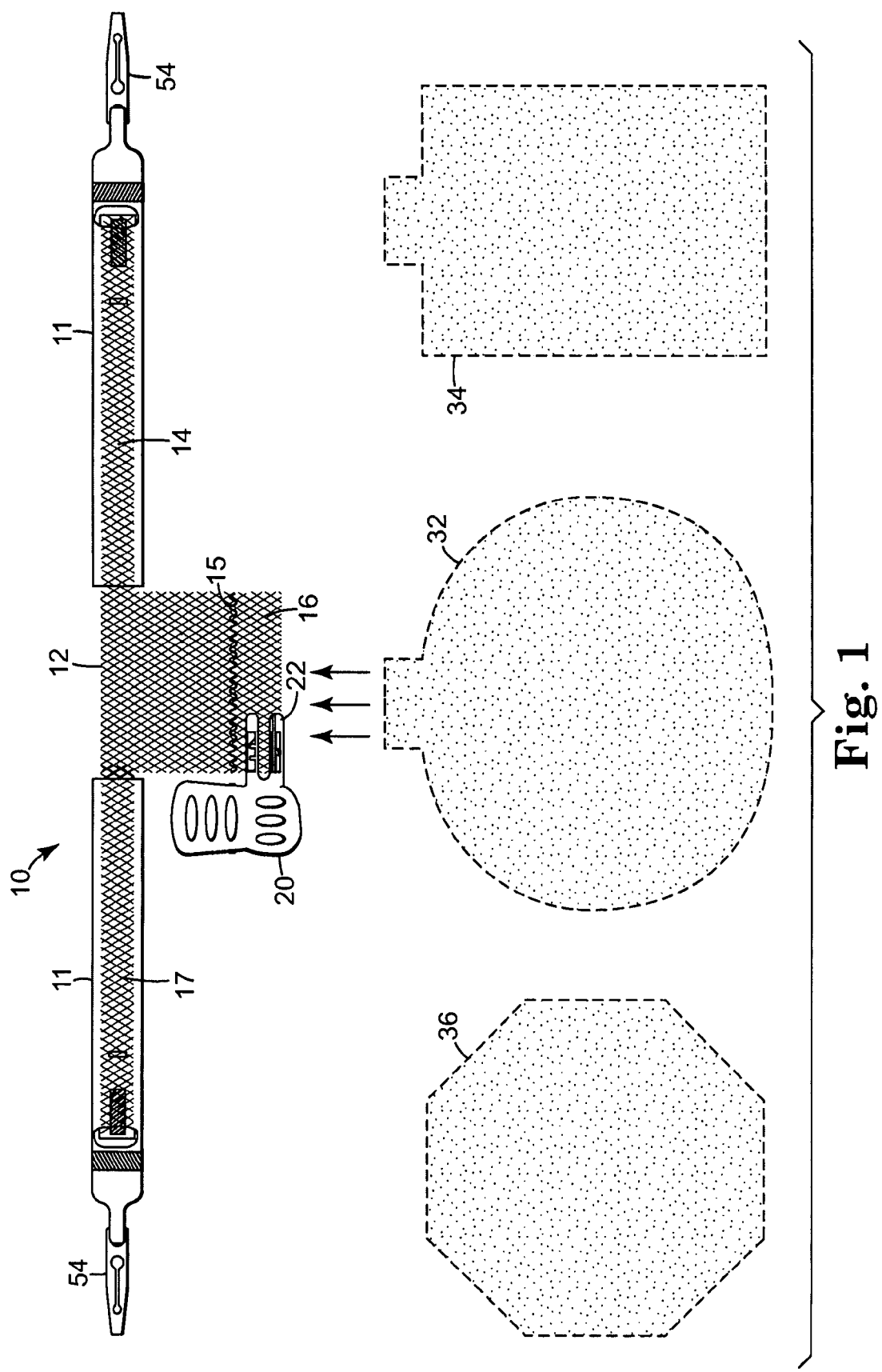
FIG. 1 is a top view of an assembly for creating a composite implant, showing three different options for a portion of the implant.
Figure 2:
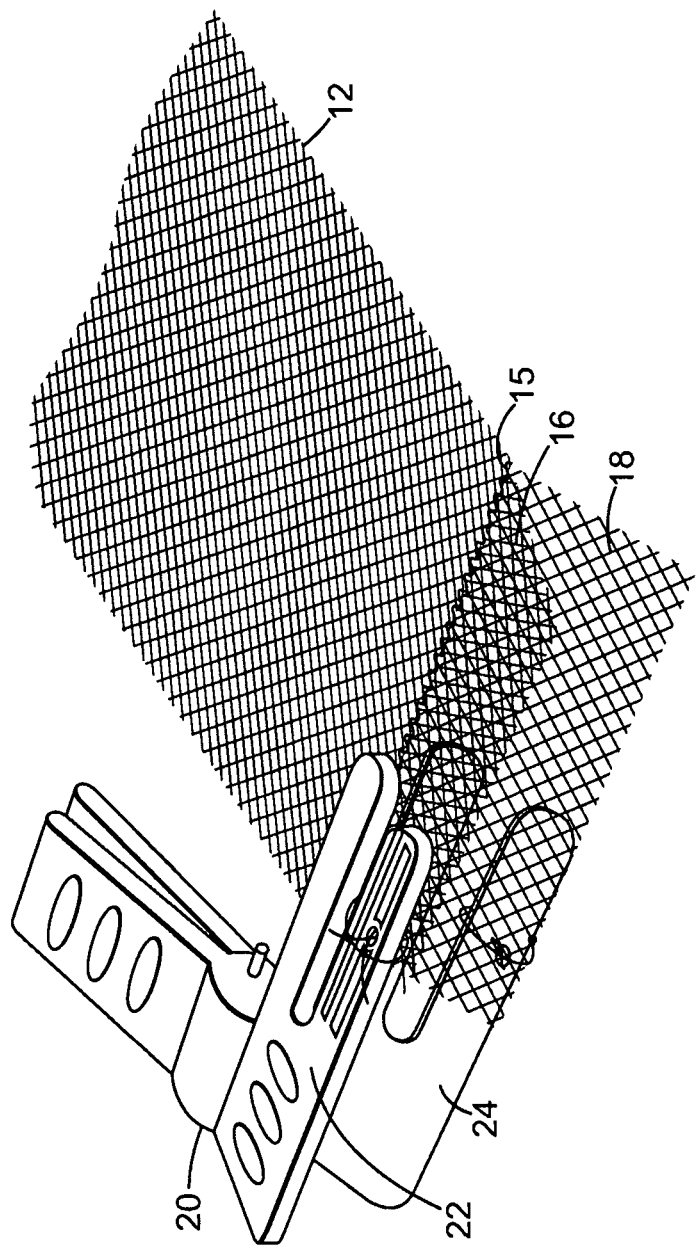
FIG. 2 is a perspective view of a portion of a component of FIG. 1, showing the component in an open position.

Referring to FIGS. 1 and 2, there is shown a modular assembly 10 for creating a customized surgical implant for treating a female patient's pelvic health disorder. The assembly includes a mesh. The mesh may be assembled from diverse materials. For example, the mesh may be assembled from a synthetic material 12 and a non-synthetic material (e.g. one of 32, 34 or 36).

The assembly 10 has a major or cystocele repair portion (e.g. 32, 34 or 36) that is sized and shaped to afford repair of a cystocele without lifting the patient's bladder and without placing undue tension on the bladder or vaginal wall. The major portions may have a predetermined size and shape. For example one major portion may be sized and shaped to correct a midline defect. Another major portion may be sized and shaped to address a lateral defect. Yet another major portion may be designed to address large defects, while another may be designed to address a small defect.

Preferably, the implant may be implanted in a tension free manner and affords tissue in-growth for vaginal wall support. Alternatively the major portion may have a portion that is sized and shaped to address a rectocele. The rectocele may be provided as an integral piece or it may be attachable.

The implant also includes a urethral support portion 12 capable of being placed underneath the patient's urethra, a first sling appendage 14 for securement on a first side of the patient's urethra; and a second sling appendage 17 for securement on a side of the patient's urethra generally opposite the first side. The urethral support portion 12 is preferably placed adjacent a mid region of the urethra in a tension free manner. Other placements are also contemplated herein such as at the bladder neck.

In one embodiment, the first sling appendage 14 is sized, shaped and configured to extend from a region near the patient's urethra to an incision in the patient's abdominal rectus fascia, on a first side of the patient's urethra, and the second sling appendage 17 is sized, shaped and configured to extend from a region near the patient's urethra to an incision in the patient's abdominal rectus fascia, on a side of the patient's urethra generally opposite the first side. In this embodiment, the width of the sling appendages 14 and 17 is preferably between 0.5 and 2 cm, more preferably between about 0.7 and 1.2 cm, more preferably about 1.1 cm. The distance between the ends of the sling appendages 14 and 17 (the transverse length) is preferably between about 40 and 60 cm, more preferably between 45 and 55 cm and even more preferably about 50 cm. As shown in FIG. 1, the implant 10 includes optional insertion sheaths 11, described in greater detail below.

In another embodiment, the first sling appendage 14 is sized, shaped and configured to extend from a region near the patient's urethra to the patient's obturator foramen, on a first side of the patient's urethra, and the second sling appendage 17 is sized, shaped and configured to extend from a region near the patient's urethra to the patient's other obturator foramen, on a side of the patient's urethra generally opposite the first side. In this embodiment, the width of the sling appendages 14 and 17 is preferably between 0.5 and 2 cm, more preferably between about 0.7 and 1.2 cm, more preferably about 1.1 cm. The distance between the ends of the sling appendages 14 and 17 (the transverse length) is preferably between about 30 and 40 cm, and even more preferably about 35 cm. Surgical tools for inserting a sling in the region of the patient's obturator foramen are disclosed in U.S. patent application Ser. No. 10/306,179, filed Nov. 27, 2002.

In a preferred embodiment, one material comprises a synthetic material (e.g. 12) and another material comprises a biomaterial (e.g. 32 in FIG. 1) or non-synthetic material. In another embodiment, one material comprises an absorbable material and the other material comprises a non-absorbable or permanent material. In another embodiment, one portion may be resorbable or absorbable, another portion may be non-absorbable and another portion may be constructed of a different material. A naturally occurring biomaterial may be used or a tissue engineered material may be used.

As used in this application, when it is said that one implant material is different than another implant material, it is meant that the materials substantially differ in a feature that can potentially affect a surgical procedure for treating a urological disorder, including the efficacy and/or results. Features that can be different according to the present invention include, but are not limited to the ability of the sling to avoid infections or tissue erosion (actual or perceived), the shelf life of the material, the type of material, the shape of the material, the presence of a sling tensioning member (e.g. as disclosed in Published U.S. Pat. Appl. No. 2002/107430-A1), the present of a sling adjustment feature (as described in U.S. patent application Ser. No. 10/004,185 filed Oct. 30, 2001), sling material treatment (e.g. heat set) or coating, the porosity of the sling material, the shape of the sling material, the strength of the material, the elastic property of the material, the potential for tissue ingrowth, the biocompatibility of the material, and the presence or absence of an insertion sheath. Examples of treatments or coatings include anti-microbials, anti-biotics or other drug coatings.

Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Suitable synthetic materials for a sling include polymerics, metals (e.g. silver filigree, tantalum gauze mesh, and stainless steel mesh) and plastics and any combination of such materials.

Commercial examples of non-absorbable materials include Marlex™ (polypropylene) available from Bard of Covington, R.I., Prolene™ (polypropylene), Prolene Soft Polypropylene Mesh or Gynemesh (nonabsorbable synthetic surgical mesh), both available from Ethicon, of New Jersey, and Mersilene (polyethylene terphthalate) Hernia Mesh also available from Ethicon, Gore-Tex™ (expanded polytetrafluoroethylene) available from W. L. Gore and Associates, Phoenix, Az., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon. Other examples of suitable materials include those disclosed in published U.S. Pat. Application No. 2002/0072694. More specific examples of synthetic sling materials include, but are not limited to polypropylene, cellulose, polyvinyl, silicone, polytetrafluoroethylene, polygalactin, Silastic, carbon-fiber, polyethylene, nylon, polyester (e.g. Dacron) polyanhydrides, polycaprolactone, polyglycolic acid, poly-L-lactic acid, poly-D-L-lactic acid and polyphosphate esters. See Cervigni et al., *The Use of Synthetics in the Treatment of Pelvic Organ Prolapse*, Current Opinion in Urology (2001), 11: 429-435.

The embodiment shown in FIGS. 1 and 2 includes an assembly tool 20. Preferably, the implant 10 includes a Y-shaped portion including legs 16 and 18 and seam 15. A suitable assembly tool is disclosed in U.S. patent application Ser. No. 10/335,119, filed Dec. 31, 2002. Alternative approaches for forming the juncture between two dissimilar materials are also disclosed in that patent application. Preferably, the seam or juncture portion 15 is preferably spaced from the portion 12 of the implant 10 for supporting the urethra so that it does not lie directly under the urethra. For example, the seam or junction 15 could be spaced between about 1 cm and about 5 cm from the edge, more preferably between 2 cm and 4 cm, more preferably about 3 cm from the parallel edge. In an alternative embodiment, the seam or junction may be placed on the major portion 32, 34 or 36 and the portion of the implant near reference character 12 could be free of any seam or juncture.

As seen in FIG. 2, the tool 20 may be used to move first and second legs 16 and 18 of the implant 10 to an open position to afford insertion of another component of the implant (e.g. 32, 34 or 36). The tool has flanges 22 and 24 that are initially attached to the legs 16 and 18 and are detachable from the legs as disclosed in the '119 application. The tool 20 affords convenient suturing of one portion of the implant to another.

Figure 27:
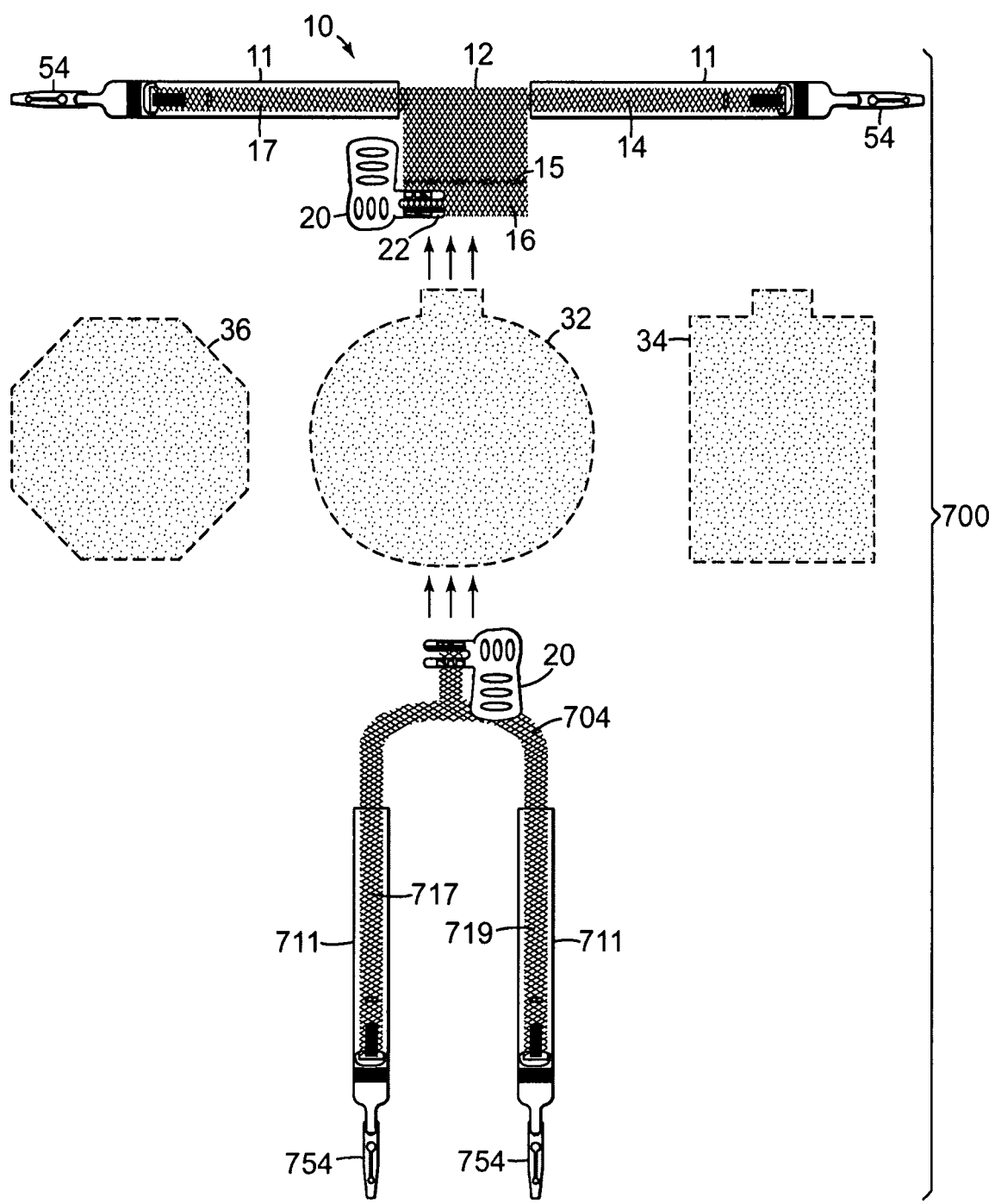
FIG. 27 is a top view of an assembly for creating a composite implant, showing an anterior portion, a major portion and a posterior portion, and showing three different options for a major portion of the implant.

FIG. 27 shows another modular assembly 700 for affording construction of a surgical implant for addressing one or more pelvic floor disorders. The assembly comprises an anterior element 10 for affording a sling-like implant. The anterior element 10 may be similar to the element 10 described with reference to FIG. 1, with like reference characters indicating like elements. Unlike the assembly of FIG. 1, the assembly 700 of FIG. 27 also includes a posterior element 704. The posterior element 704 includes distal end portions 717 and 719 for securement in a posterior region of the patient's body. Optional insertion sheaths 711 and dilating connectors 754 may also be utilized.

The assembly 700 also includes a mid-portion or cystocele repair portion 32, 34 or 36 for affording repair of a cystocele. As depicted, the cystocele repair portion may be associated with either the anterior element or the posterior element or both elements. Preferably the assembly includes a means for facilitating association between elements of the assembly such as tools 20. Alternatively the tools 20 may be placed on the mid portion 32, 34 or 36 of the assembly 700 instead of the anterior and posterior portions. Also preferably, the cystocele repair portion includes indicia to facilitate trimming to adjust the implant to different sizes. A rectocele repair portion may also be provided. In alternative embodiments, the rectocele repair portion may be connected to the posterior portion 704 or the cystocele repair portion 32, 34 or 36.

Figure 3:
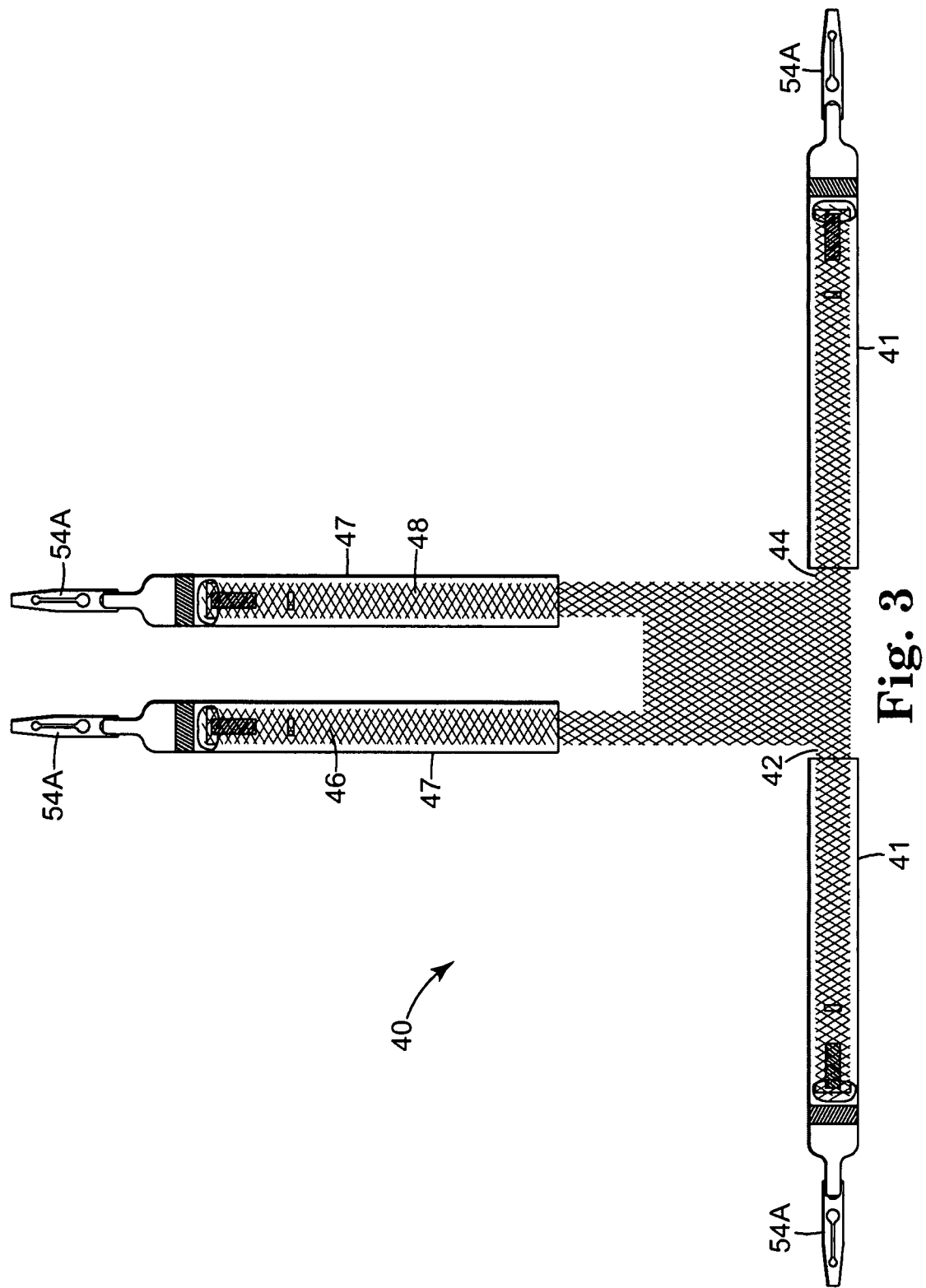
FIG. 3 is top view of another embodiment of implant according to an aspect of the present invention.

Referring to FIG. 3, there is shown another embodiment of implant 40 according to the present invention. The implant 40 includes first and second sling appendages 42 and 44 and a portion adapted to be secured in the patient's vaginal region. The implant also has a first posterior securement appendage 46 that is sized, shaped and configured to extend from the patient's vaginal region toward a first incision in the patient's buttocks and lateral to the patient's anus; and a second posterior securement appendage 48 that is sized, shaped and configured to extend from the patient's vaginal region, on a side of the patient's anus different than that of the first posterior securement appendage, toward a second incision in the patient's buttocks that is on a side of the patient's anus opposite the first incision. Preferably, the first and second posterior securement appendages 46 and 48 have distal end regions adapted to be secured in the patient's ischioanal fossa or ischiorectal fossa. Alternatively, instead of the linear edges shown in FIG. 3, the securement appendages may include curved edges to provide arced or curved shaped appendages.

The implant 40 also preferably includes dilating connectors 54A. Suitable dilating connectors are disclosed in Published U.S. Pat. Application Nos. 2002/151762 and 2002/147382 and U.S. patent application Ser. No. 10/386,897, filed Mar. 11, 2003.

In one embodiment, the portion of the synthetic implant 40 designed to remain in vitro may comprise a mesh material. The mesh material comprises one or more woven, knitted or inter-linked filaments or fibers that form multiple fiber junctions throughout the mesh. The fiber junctions may be formed via weaving, molding, knitting, braiding, bonding, punching, ultrasonic welding or other junction forming techniques, including combinations thereof. In addition, the size of the resultant openings or pores of the mesh may be sufficient to allow tissue in-growth and fixation within surrounding tissue.

A wide variety of factors affect an implant material's longitudinal extensibility. The quantity and type of fiber junctions, yarn knit, fiber weave, pattern, and material type influence various sling properties or characteristics. Other factors include heat set of the individual strands, the degree of tension at heat setting of the monofilaments, the diameter of the monofilament yarn, the bar settings on the knitting machine, coatings and finishes.

Figure 4:
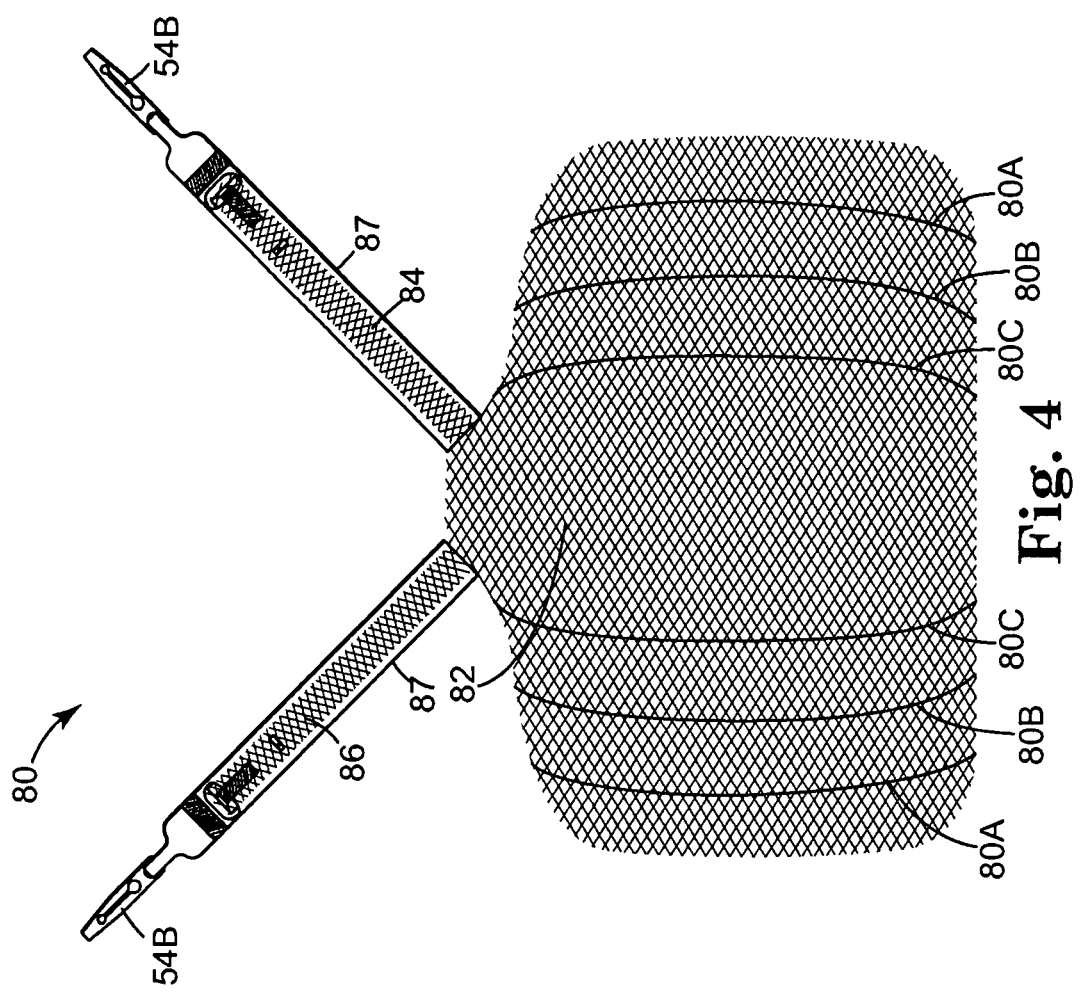
FIG. 4 is a top view of another embodiment of implant.

Referring to FIG. 4, there is shown another embodiment of implant 80 according to the present invention. The implant comprises a synthetic mesh material that has a portion 82 adapted to be secured in the vaginal wall region via a vaginal incision. The synthetic mesh has incremental indices 80A, 80B and 80C that can be used as a guide to trim to specific anatomical requirements for lateral and/or central defects. The implant 80 has a first posterior securement appendage 86 that is sized, shaped and configured to extend from the patient's vaginal region toward a first incision in the patient's buttocks and lateral to the patient's anus; and a second posterior securement appendage 84 that is sized, shaped and configured to extend from the patient's vaginal region, on a side of the patient's anus different than that of the first posterior securement appendage, toward a second incision in the patient's buttocks that is on a side of the patient's anus opposite the first incision. Preferably, the first and second posterior securement appendages 86 and 84 have distal end regions adapted to be secured in the patient's ischioanal fossa or ischiorectal fossa.

The implant 80 is preferably constructed from a longitudinally extensible material. Optionally, the implant 80 utilizes insertion sheaths 87 for the first and second posterior securement appendages 86 and 84. Also, the implant 80 preferably includes dilating connectors 54B adapted to associate the implant 80 with the distal end of an insertion needle.

The implant 80 is particularly suitable for accommodating varying degrees of cystocele repairs for a central and lateral (white line) support. For example, the ends of the portion 82 may be sized and shaped to be sutured to the patient's arcus tendeneus (white line). Alternatively, if such support is not required, the ends of the portion 82 could be secured to the sacrospinous ligaments, the levator ani tissues, the uterosacral ligaments.

In a preferred embodiment, the implant 80 is inserted through a vaginal incision. The posterior appendages are used to secure the vault by being pulled through the ischiorectal fossa while the mid portion is secured to the vaginal tissue. Optionally, the appendages may be preattached to the cystocele patch portion or may be provided as a portion of a composite assembly, similar to assembly 10. Also, instead of the straight appendages shown, another embodiment may comprise curved appendages.

The indica or markings 80A, 80B and 80C are preferably spaced a predetermined distance from an edge of the implant 80. The indicia 80A, 80B and 80C afford convenient, symmetrical trimming that can save surgical time. Alternatively, instead of the curved shape, the indicia 80A, 80B, 80C may comprise linear markings.

In another embodiment, the first sling appendage 86 may be sized, shaped and configured to extend from a region near the patient's urethra to the patient's obturator foramen, on a first side of the patient's urethra, and a second sling appendage 84 may be sized, shaped and configured to extend from a region near the patient's urethra to the patient's other obturator foramen, on a side of the patient's urethra generally opposite the first side.

Figure 5:
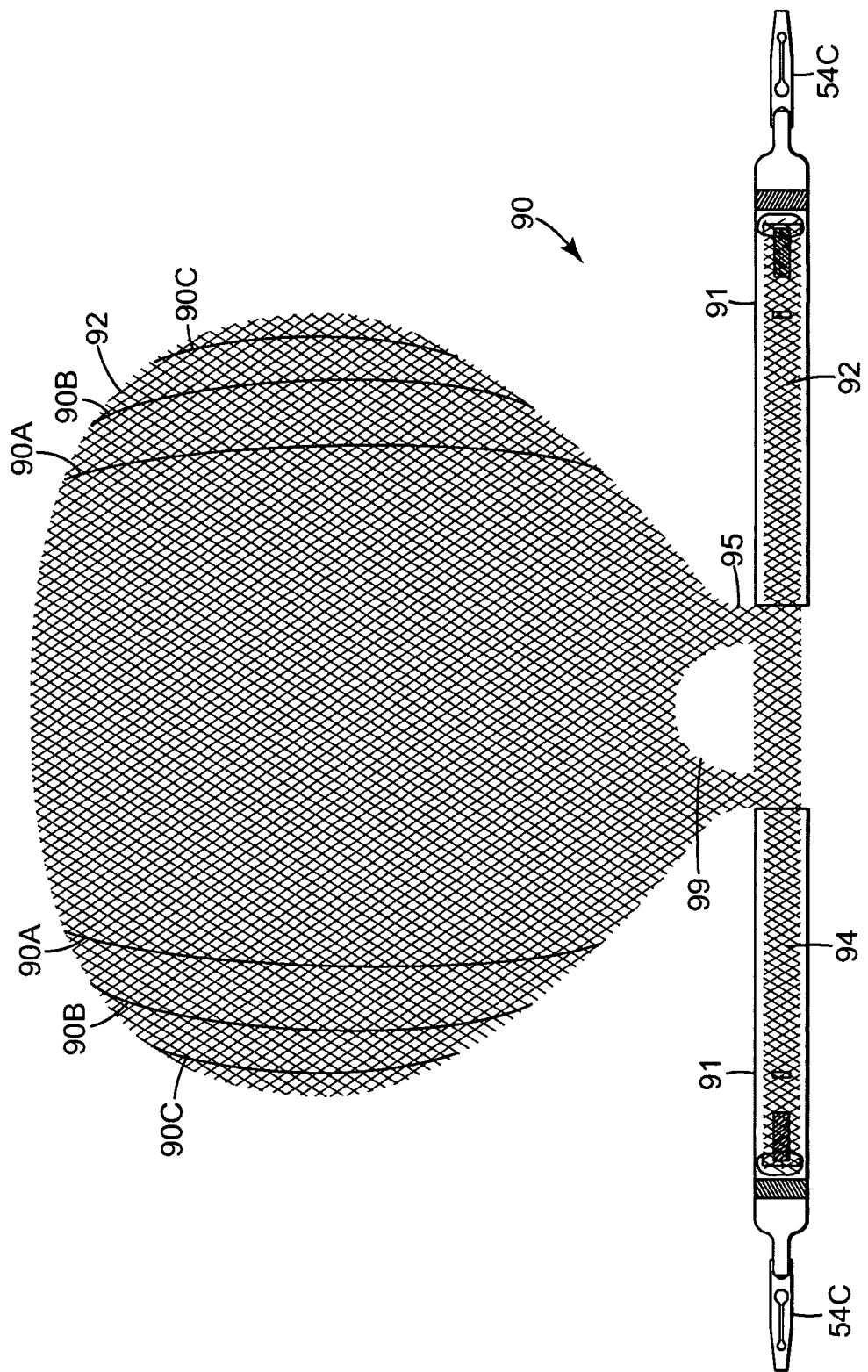
FIG. 5 is a top view of another embodiment of implant.

Referring to FIG. 5, there is shown another embodiment of implant 90 according to the present invention. The implant 90 comprises a synthetic mesh material that has a major portion 95 adapted to be secured in the vaginal wall region (e.g. the vaginal apex or cuff), preferably via a vaginal incision. The synthetic mesh has incremental indices 90A, 90B and 90C that can be used as a guide for trimming to specific anatomical requirements for lateral and/or central defects. The major portion 95 also includes a urethral support portion capable of being placed underneath the patient's urethra.

The implant 90 includes a first sling appendage 94 for securement on a first side of the patient's urethra; and a second sling appendage 92 for securement on a side of the patient's urethra generally opposite the first side. The first sling appendage 94 is sized, shaped and configured to extend from a region near the patient's urethra to an incision in the patient's abdominal rectus fascia, on a first side of the patient's urethra, and the second sling appendage 92 is sized, shaped and configured to extend from a region near the patient's urethra to an incision in the patient's abdominal rectus fascia, on a side of the patient's urethra generally opposite the first side.

A hole 99 may be provided in the implant 90 to afford convenient conformation of the implant 90 to irregular anatomical structures. Optionally, the hole 90 may be situated to encompass the vaginal incision used to insert the implant 90 to avoid any contact between the implant 90 and the incision.

In another embodiment, the first and second sling appendages are sized, shaped and configured to extend from a region near the patient's urethra to and/or through the patient's obturator foramen.

Figure 6:
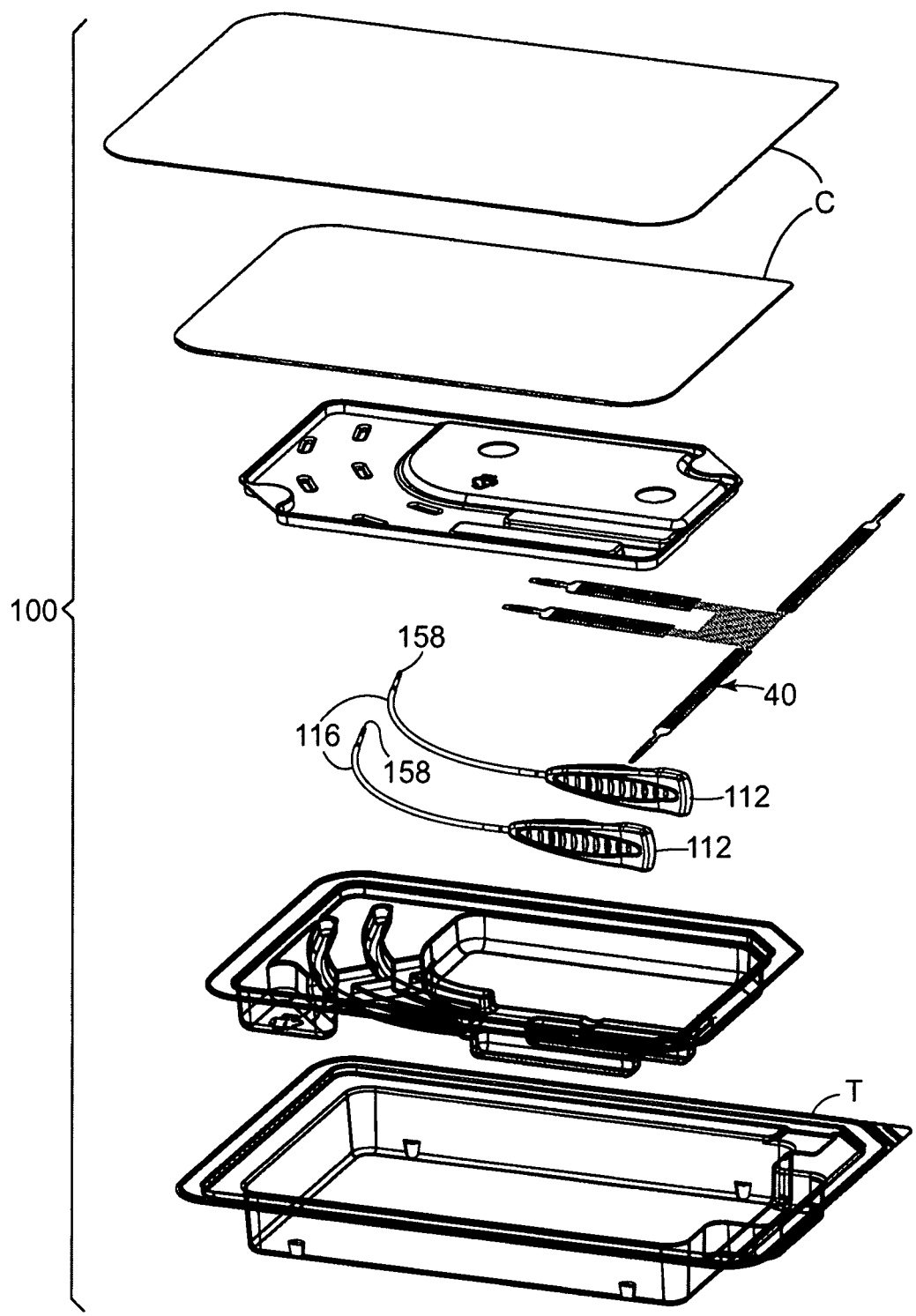
FIG. 6 is an exploded perspective view of a surgical kit according to another aspect of the present invention.

Referring to FIG. 6, in another aspect, the present invention comprises a surgical kit or assembly 100. The assembly 100 includes first and second insertion needles 116 and a longitudinally extendible implant capable of being secured in the posterior region of the patient's body.

In another embodiment of surgical kit according to the present invention, third and fourth insertion needles (not shown in FIG. 6) may also be provided. These needles may be substantially similar to the first and second insertion needles or they may be different. For example, the third and fourth insertions needles may be designed for a specific surgical approach (e.g. transobturator or suprapubic).

The first and second insertion needles 116 are configured so that their distal ends 158 may be initially inserted through an incision in the patient's buttocks and then passed through tissue, emerging through a vaginal incision. The first and second insertion needles preferably have an outer diameter of less than about 4 mm, more preferably less than about 3.3 mm to minimize tissue disruption and damage.

The implant provided with the kit comprises a synthetic mesh material with a portion adapted to be secured in the patient's vaginal region (preferably by virtue of a suture that does not go through the vaginal mucosa), a first posterior securement appendage that is sized, shaped and configured to extend from the patient's vaginal region toward a first incision in the patient's buttocks and lateral to the patient's anus; and a second posterior securement appendage that is sized, shaped and configured to extend from the patient's vaginal region, on a side of the patient's anus different than that of the first posterior securement appendage, toward a second incision in the patient's buttocks that is on a side of the patient's anus opposite the first incision.

Preferably, the portion of the implant adapted to be secured in the patient's vaginal region is adapted to be sutured to the patient's vaginal apex. The implant 40 of FIG. 6 is a relatively complex shape, but alternatively, referring to FIG. 25 the implant can comprise a substantially rectangular, longitudinally extendible implant material 944 with first and second flexible insertion sheaths. The kit of FIG. 25 preferably includes dilating connectors 954 and at least two, relatively small (i.e. outer diameter less than about 4 mm) needles 960.

While the implant 40 depicted in FIG. 6 is preferably constructed from a longitudinally extendable material, it is within the scope of the present invention to provide a kit comprising an inextensible implant and at least two posterior implantation needles.

A surgical kit 100 according to the present invention may optionally include additional accessories. For example, a surgical drape specifically designed for urological procedures such as a sling procedure may be included in a kit of the present invention. Such a drape is disclosed in published U.S. Pat. Appl. No. 2002-078964-A1. Alternatively, an article for objectively setting tension of the sling, such as one of the articles described in U.S. patent application Ser. No. 09/968,239, filed Oct. 1, 2001 may be included in the kit.

The kits 100 preferably include at least two needles. In various embodiments of the present invention, the needles may comprise the needles described in published U.S. Pat. Application Nos. 20023-0065246-A1; 2002-0151762-A1; 2002-0147382-A1; 2002-0107430-A1, US-2002-0099258-A1 and US-2002-0099259-A1; and U.S. Provisional Application Ser. Nos. 60/263,472, filed Jan. 23, 2001; 60/269,829, filed Feb. 20, 2001; 60/281,350, filed Apr. 4, 2001; 60/295,068, filed Jun. 1, 2001; 60/306,915, filed Jul. 20, 2001, and 60/332,330, filed Nov. 20, 2001. In an embodiment that is particularly suitable for a transobturator surgical procedure, the needles comprise needles as described in U.S. patent application Ser. No. 10/306,179 filed Nov. 27, 2002.

The outer diameter of the optional dilators is also preferably small and may comprise the dilators disclosed in U.S. patent application Ser. No. 10/386,897 filed Mar. 11, 2003.

In some instances the needles may be substantially identical, in other instances, they may be different. Two or more needles reduce the need to reuse a non-sterile needle at a different location with a patient, thereby eliminating cross contamination issues. Additional needles, handles, dilators and other elements may also be included for surgical convenience, for avoidance of contamination from one portion of the body to another, for ease of manufacturing or sterilization or for surgical requirements.

The individual elements of the kits of the present invention may be packaged together as shown in FIG. 6 with a cover C and tray T. Alternatively, the individual elements may be separately packaged or packaged in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), gamma or plasma procedures.

The above-described insertion needles may be disposable or reusable. They may be malleable (manually bendable) or rigid. Optionally, portions of the insertion needles may be reusable (sterilizable) and other components may be disposable.

Figure 26:
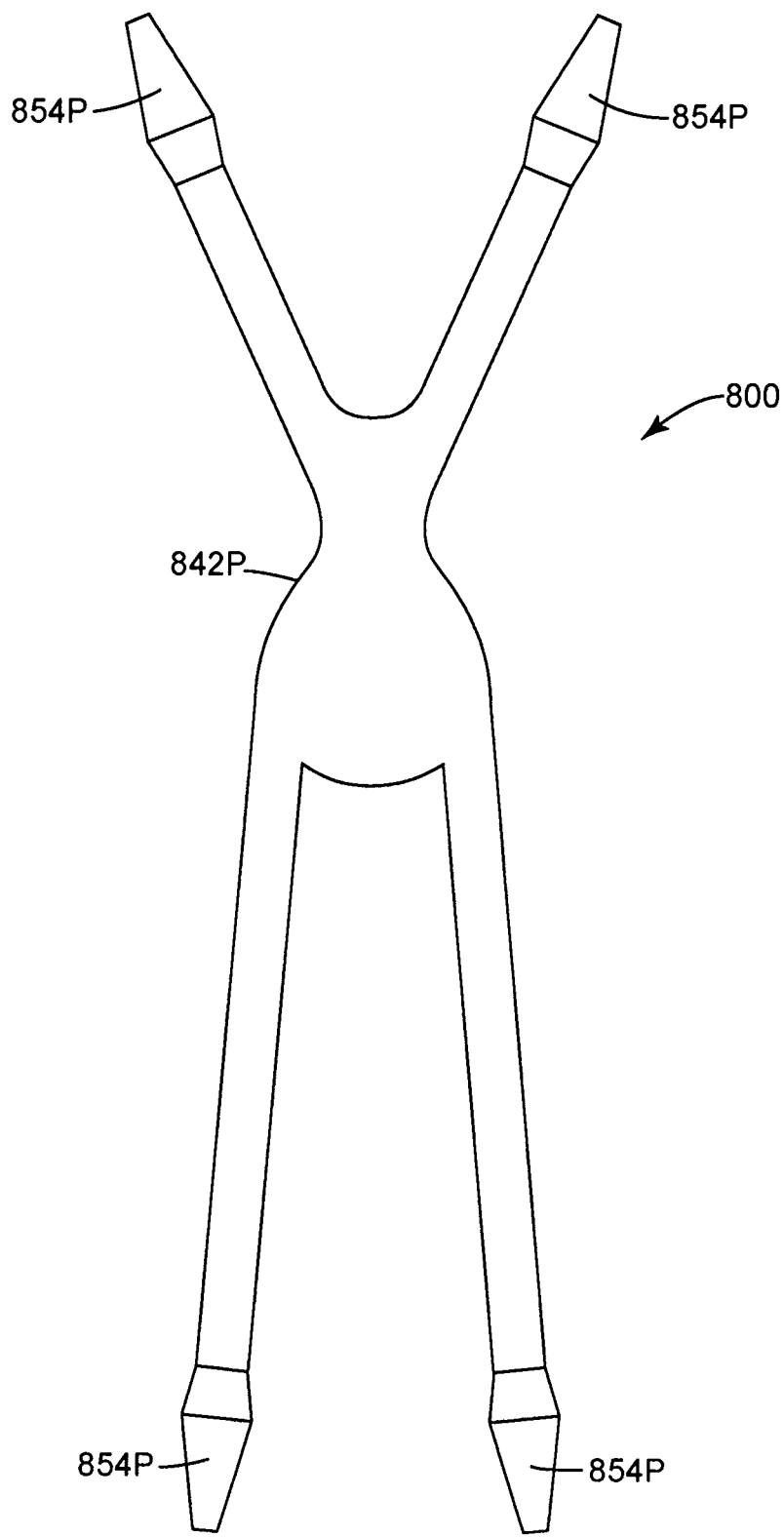
FIG. 26 is a top view of another embodiment of the present invention.

FIG. 26 shows another embodiment of implant assembly 800 according to the present invention. The implant assembly 800 comprises a synthetic mesh having a major portion 842P, and at least four projections extending from the major portion 842P. The implant assembly 800 may be used as a hammock to support the bladder or for other procedures to address a cystocele or prolapse or a vaginal vault treatment. Each of the projections preferably has a dilating connector 854P associated with a distal end. The projections may be implanted via transobturator, suprapubic or posterior techniques. For example, one of the projections may be placed on a first side of the patient's urethra and extend from the patient's urethral region to the patient abdominal rectus fascia, and another of the projections is adapted to be placed on a side of the patient's urethra generally opposite the first side.

As another example, one of the projections may be anchored in the patient's right obturator foramen, another of the projections may be anchored in the patient's left obturator foramen and the other two projections may extend to the patient's rectus abdominus fascia. Various anchoring techniques may be utilized including those disclosed in published U.S. Patent application No. 2002/0161382-A1. In this embodiment, the central portion of the implant 800 may be secured in the vaginal region for vaginal vault or cystocele repairs.

In yet another embodiment, two of the projections may be anchored in the patient's left obturator foramen and the other two projections may be anchored in the patient's right obturator foramen. The central portion may be secured in the vaginal region to address pelvic disorders.

Figure 14:
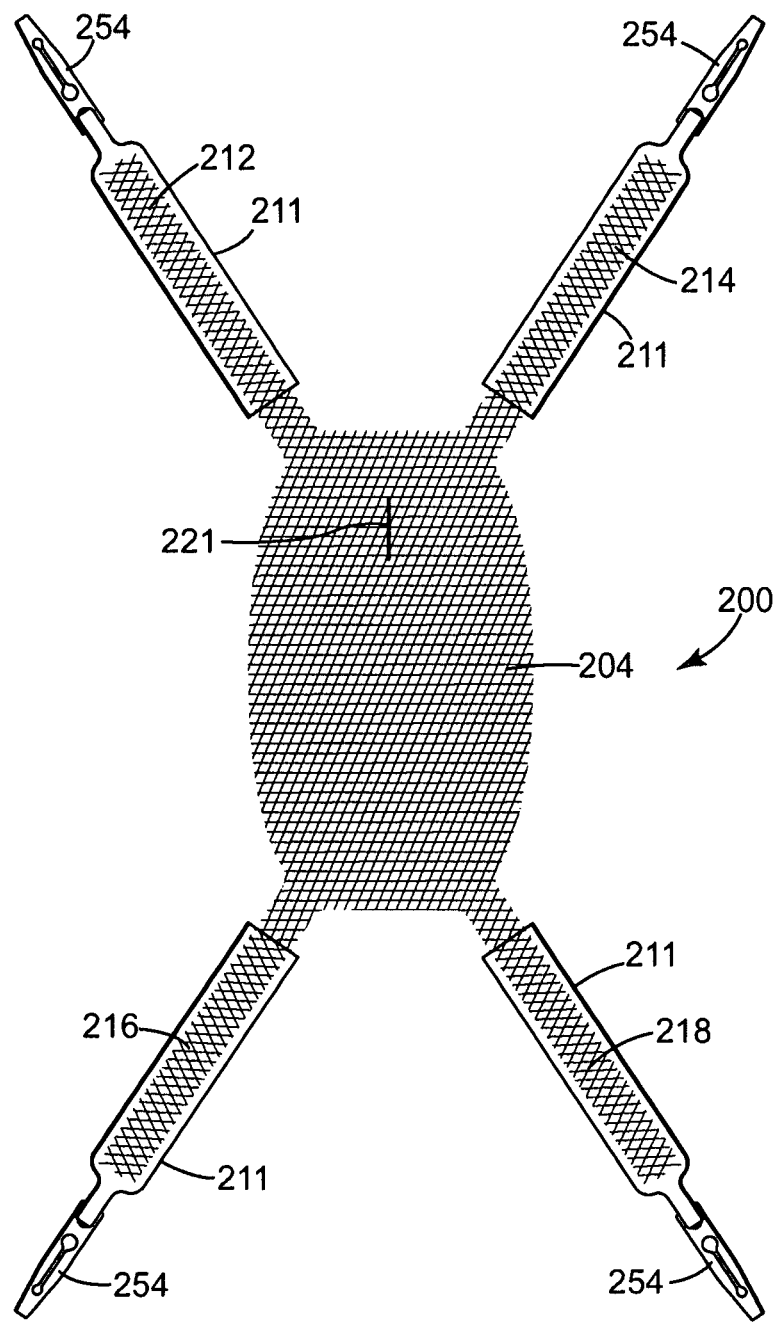
FIG. 14 is a top view of another embodiment of implant.

Referring now to FIG. 14, there is shown another embodiment of implant 200 according to the present invention. The implant 200 includes a synthetic mesh material having a portion 204 adapted to be secured in the patient's vaginal region, a first posterior securement appendage 212 that is sized, shaped and configured to extend from the patient's vaginal region toward a first incision in the patient's buttocks and lateral to the patient's anus; and a second posterior securement appendage 214 that is sized, shaped and configured to extend from the patient's vaginal region, on a side of the patient's anus different than that of the first posterior securement appendage, toward a second incision in the patient's buttocks that is on a side of the patient's anus opposite the first incision. Optionally, the implant 200 may include a first flexible insertion sheath 211 associated with at least a portion of the first posterior securement appendage, and a second flexible insertion sheath 211 associated with at least a portion of the second posterior securement appendage 214.

The implant 200 also includes a first sling appendage 216 for securement on a first side of the patient's urethra; and a second sling appendage 218 for securement on a side of the patient's urethra generally opposite the first side of the urethra. Optional insertion sheaths 211 may also be utilized.

The implant 200 may also include dilators 254 (e.g. as disclosed in published U.S. Pat. Appl. No. 2002/151762-A1). Preferably, the dilators 254 include a connector for connecting to the distal end of a surgical needle.

In a preferred embodiment, the first and second posterior securement appendages 212 and 214 have distal end regions adapted to be secured in the patient's ischioanal fossa or ischiorectal fossa. Alternatively, the first and second posterior securement appendages have distal end regions adapted to be secured in the patient's sacrospinous ligaments, the uterosacral ligaments, or the levator ani muscles. Preferably, the connectors include surfaces for dilating tissue.

The implant 200 also preferably includes a slit or slot 221. The slit 221 may help the implant 200 conform to irregular surfaces such as the vaginal apex or cuff. Alternatively, the slit may be designed to form a hole when the implant conforms to an irregular surface. In a preferred embodiment, that hole can be situated to encompass the vaginal incision used to insert the implant 200 to avoid post implantation contact between the implant 200 and the surgical incision.

The portion 204 is preferably sized and shaped to afford cystocele repairs. The maximum width of the central portion 204 is preferably between about 2 and 20 cm, and the length is also between about 2 and 20 cm. Markings may be provided to afford trimming in a symmetrical fashion or to provide strategic slits for conforming the implant to an irregular surface. A 6 inch×6 inch or 15 cm×15 cm central portion are within the scope of an aspect of the present invention. The appendages 212, 214, 216 and 218 may have the widths and lengths similar to the width and length ranges described with reference to previous embodiments. As an example, the length between distal ends of the appendages 212 and 214 as measured along their longitudinal axis and across a portion of central portion 204 is preferably between about 40 and 55 cm. The width is preferably between 0.5 and 1.5 cm. The length between distal ends of the appendages 216 and 218 as measured along their longitudinal axis and across a portion of central portion 204 may be slightly less than that of the appendages 212 and 214. For example, the length may be between about 25 cm and 50 cm, more preferably about 38 cm in length. The width may also be less, preferably between about 0.4 cm and about 1.2 cm.

In another embodiment of the invention of FIG. 14, the appendages 214 and 218 may be sized and shaped to extend to and/or through the patient's left obturator foramen, and the appendages 212 and 216 may be sized and shaped to extend to and/or through the patient's left obturator foramen. In this embodiment, both appendages 214 and 218 may be attached to a single dilator instead of two separate dilators in FIG. 14. Correspondingly, both appendages 212 and 216 may likewise be attached to a single dilator.

The appendages may project from the longitudinal axis of the major portion 204 at an angle between 0 and 90 degrees. Additionally, instead of the substantially rectangular, straight appendages, the appendages may be curved.

The implant 200 may be substantially symmetrical about its longitudinal axis. In some embodiment, the implant 200 may be asymmetrical about an axis transverse to the longitudinal axis. The implant may include indicia 208 indicating an appropriate position for trimming. If the implant is not symmetrical or would require a particular orientation (e.g. for the slit 221 to encompass the vaginal apex), the indicia 208 may include text or other symbols indicating the proper orientation (e.g. posterior or anterior).

Figure 15:
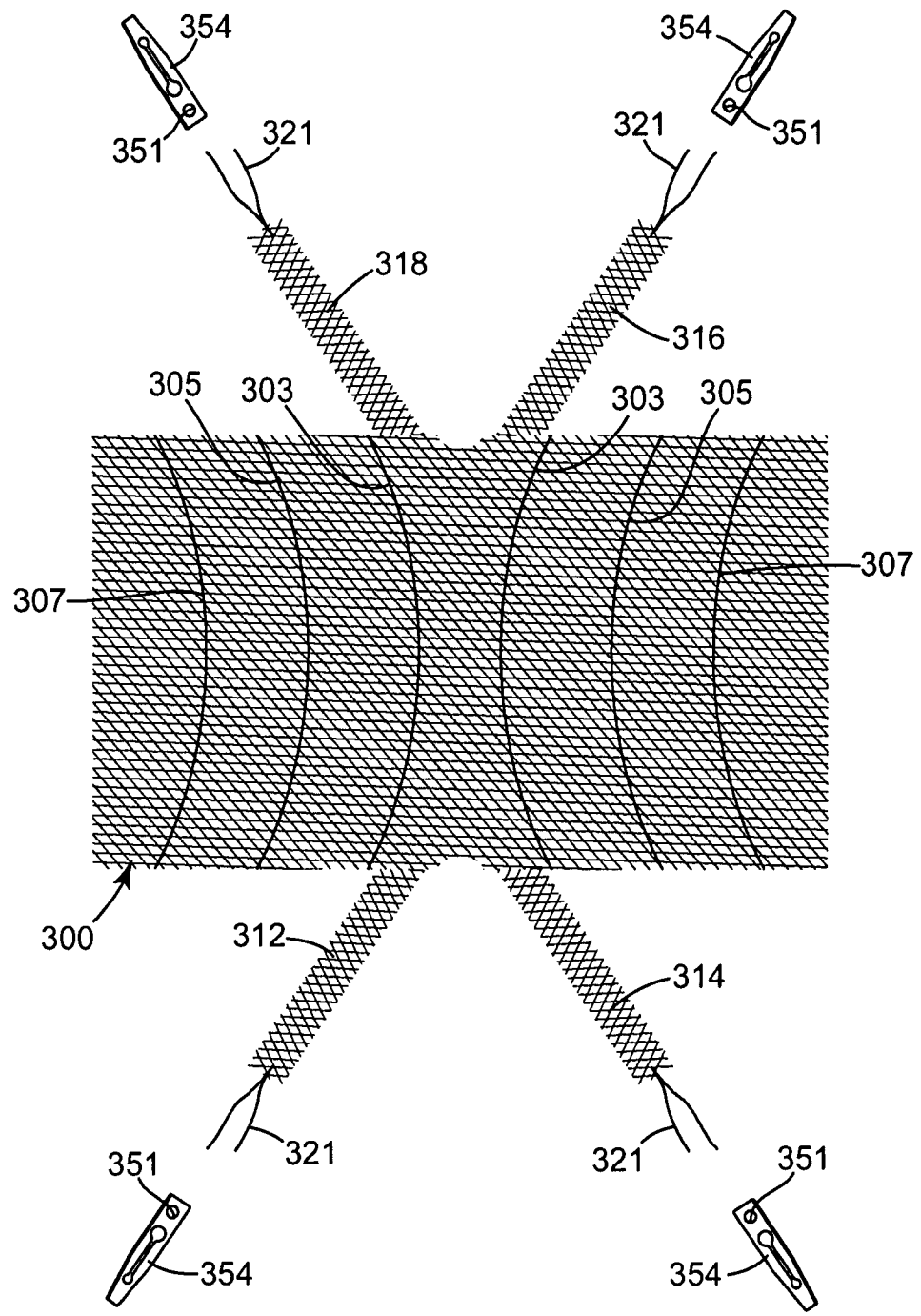
FIG. 15 is a top view of another embodiment of implant.

FIG. 15 shows a unitary, modular implant 300. The implant 300 includes projections 312, 314, 316, 318 and a major portion with indicia 303, 305, 307. The indicia and size and shape of the implant 300 allow the surgeon to conveniently choose a portion of the graft for single and/or multiple repairs. For example, a bladder tape sling procedure can be accomplished either through a transobturator needle approach or suprapubic needle approach. The central portion can be trimmed to repair a central or lateral anterior vaginal wall repair. The demarcations 303, 305 and 307 can be utilized to help symmetrically trim either side to attach or lay a portion of the implant along the white line or arcus tendinae. The indicia may also be used to indicate strategic positions for slits to be placed to help the implant conform to an irregular surface. While the indicia 303, 305 and 307 are shown as arcuate lines, other shapes, such as straight lines, are also within the scope of the present invention.

The posterior appendages 312 and 314 can be used to restore apical support by attaching the vaginal cuff to the mesh and pulling the appendages through rectal fascia to pull the apex back via the ischiorectal fossa needle passage or via the transobturator needle passage. The graft materials for the appendages or portions thereof may or may not be the same material as the central-portion depending on the preferred mesh properties for each repair. The middle portion of the graft 300 is preferably an open mesh knit to afford a supple and compliant graft in the anterior vaginal wall that allows tissue ingrowth. The appendages also preferably afford tissue ingrowth to afford anchoring in the fascia for bladder and vault support. The graft material 300 preferably has some demarcations 335 at the appendage sites as well as along the mid portion of the graft that can be used to identify where the surgeon can cut depending on what type of repair is to be conducted.

The implant 300 depicted in FIG. 15 does not include insertion sheath to point out that some complex shaped implants of the present invention could be constructed from a material that does not readily elongate under longitudinal forces. While not preferred, such an implant may be implanted by the use of preattached sutures 321 (described below).

The present invention contemplates a variety of different sizes and shapes for the central portion of the implant 300. As an example, not intended to be limiting, the central portion may comprise a 6 inch×6 inch mesh. Other sizes are also contemplated (e.g. a 12 cm×12 cm central portion, as the distance from one ischial spine to another is often about 9-10 cm). Alternatively, instead of a square or rectangular shaped central portion, the edges may be curved.

The implant 300 may be constructed from a longitudinally extendable or longitudinally non-extendable material. Optionally, sutures 321 may be preattached to the appendages 312, 314, 316 and 318. The sutures 321 may be used to secure the implant 300 in the pelvic region. Alternatively, the sutures may connect an appendage to an insertion needle (e.g. with an eyelet or fish-hook shaped slot) to afford insertion of the implant. If a longitudinally extendable material is used, insertion sheaths may be provided for the appendages 312, 314, 316 and 318.

Optional dilators 354 are shown. The dilators include holes 351. Sutures 321 may be tied in holes 351 to afford association with the dilators 354. Notably, the sutures 321 for appendages 314 and 316 could be tied in the hole 351 of a single dilator 354 and then passed to the patient's obturator foramen. Other associations between an implant material, sutures, sheaths and dilator are contemplated herein including those shown in published U.S. Pat. Appl. No. 2002/147382-A1 and U.S. patent application Ser. No. 10/386,897, filed Mar. 11, 2003.

Figure 16:
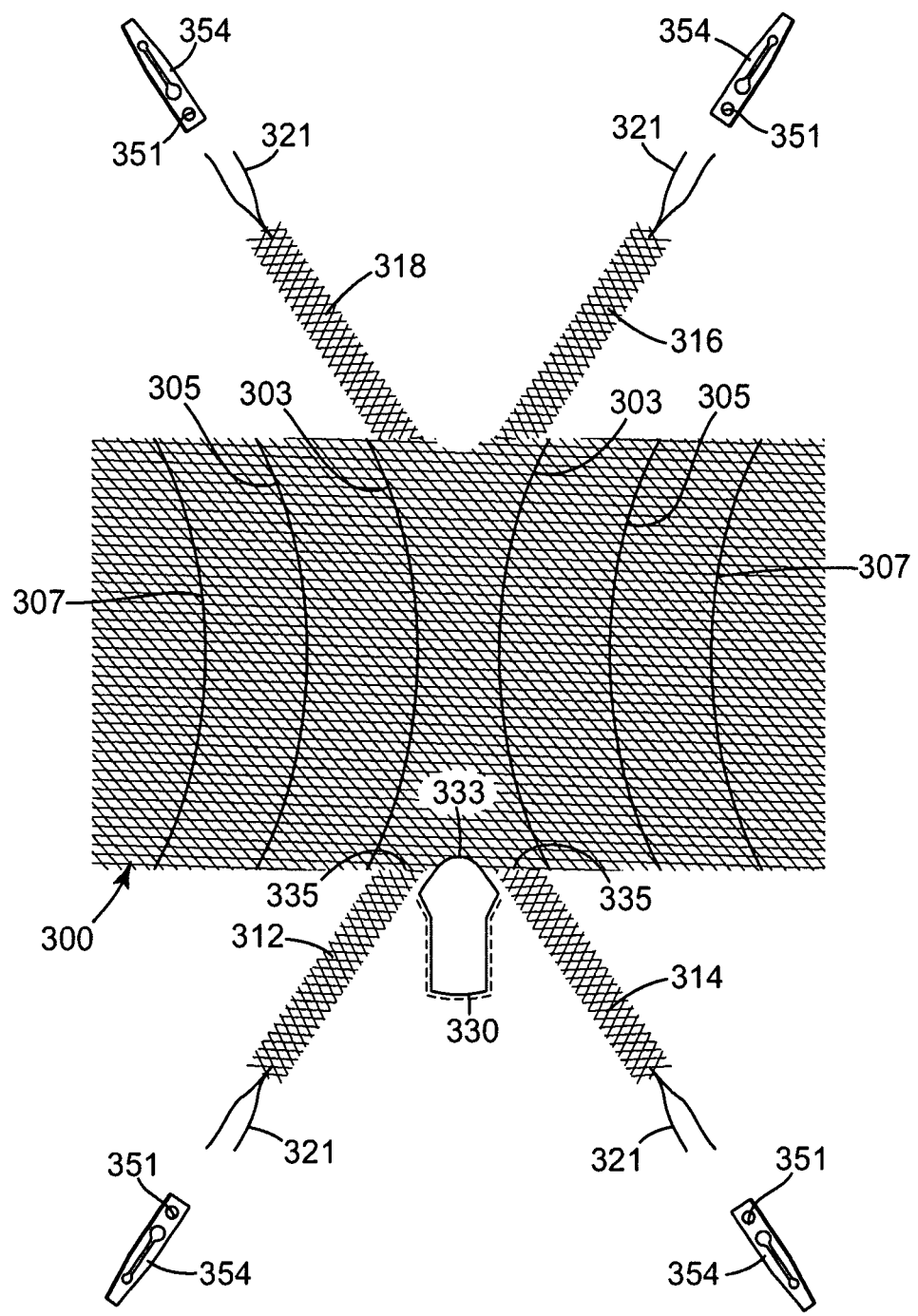
FIG. 16 is a top view of another embodiment of implant similar to FIG. 15 with an additional element shown in phantom lines.

Referring to FIG. 16, there is shown an implant substantially identical to that of FIG. 15, with like reference characters in FIG. 16 being substantially the same as the elements of the implant shown in FIG. 15. Unlike FIG. 15, the implant shown in FIG. 16 a portion 330 that is sized and shaped to afford a concomitant rectocele repair. The portion 330 may, for example have a length of about 6 cm.

Another embodiment of implant 440 is shown in FIGS. 17 and 18. The implant includes first and second sling portions 442 and 444. Preferably, the implant 440 includes insertion sheaths 441 and dilating connectors 454, but these may be omitted (e.g. if the implant is constructed form a suitable material). The implant 440 includes a mid portion 443 and flap 458 secured to the mid portion 443 along junction 445.

The implant 440 also includes first and second posterior securement appendages 446 and 448, preferably sized and shaped to be placed in the patient's ischioanal fossa or ischiorectal fossa. Optional insertion sheaths 447 and dilating connectors 454A may be provided.

Figure 19:
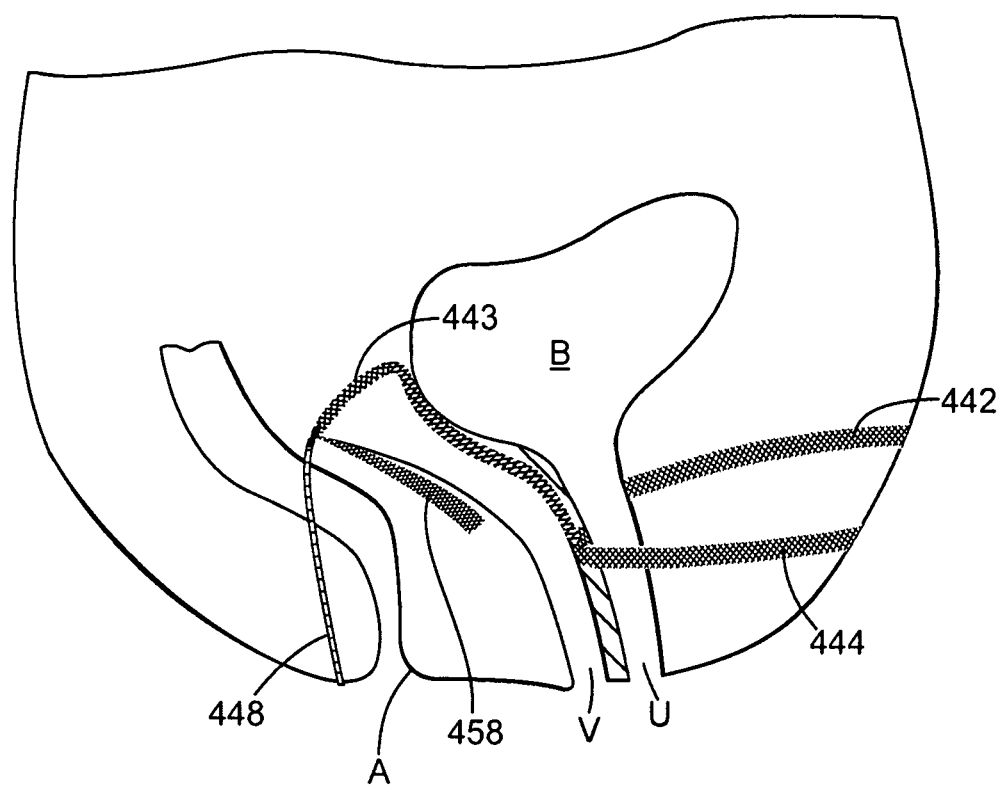
FIG. 19 is a schematic view of the implant of FIG. 17 implanted in vitro.

FIG. 19 schematically illustrates the implant 443 after implantation. The sling appendages 442 and 444 are preferably placed mid-urethra in a tension free manner. Alternatively, the sling appendages 442 and 444 may be placed at the bladder neck. The posterior securement appendage 446 (not shown in FIG. 19) and 448 are placed in the patient's buttocks region (e.g. ischia fossa) on opposite sides of the patient's anus A. The view is slightly distorted to illustrate certain details. For example, the posterior securement appendage 448 preferably exits at or about the level of the anus A, not above it as shown. The flap 458 and mid portion 443 are placed about the vaginal apex and can be secured by suturing to the vaginal tissue.

Figure 20:
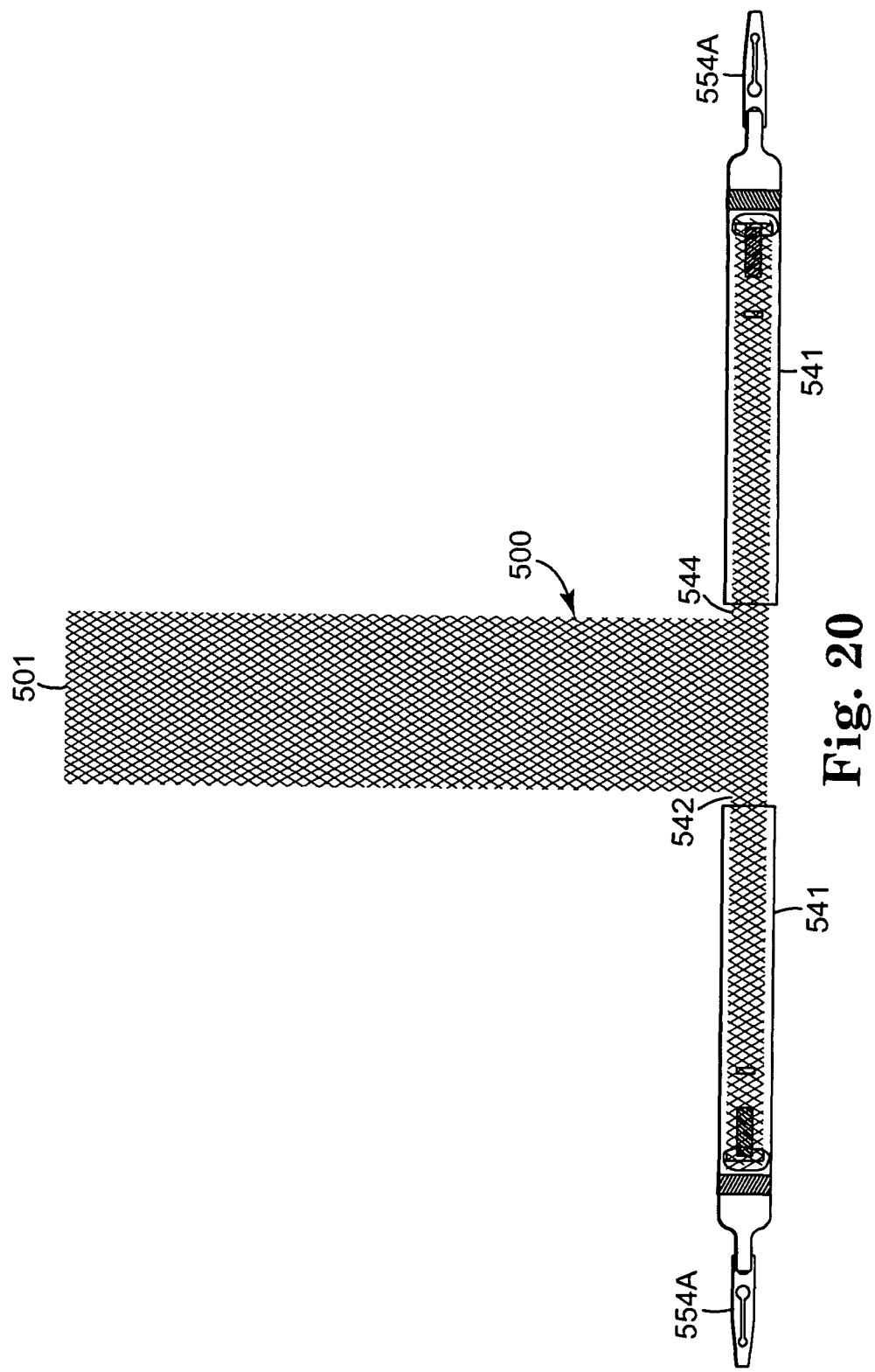
FIG. 20 is a top view of another embodiment of implant according to the present invention.

FIG. 20 shows another embodiment of implant 500 according to the present invention. The implant includes sling appendages 542 and 544 and optional insertion sheaths 541 and dilator connectors 554. Unlike implants with posterior securement appendages designed for implantation in the patient's buttocks, the implant 500 includes a portion having an end 501 that may be secured to the patient's sacrum (e.g. via bone anchors with associated sutures as shown in Published U.S. Pat. App. No. 2002/0028980) so that a combination sacral colpopexy and sling procedure can be accomplished with a single implant 500. Optionally, the implant 500 includes a flap similar to the flap 458 shown in FIGS. 17-18. The length of the implant between end 501 and an opposite end may be between about 6 and 12 inches, more preferably between 8 and 12 inches. The width of end 501 is preferably between 0.75 and 2 inches wide. The optional flap may be situated between about 4 and 6 inches from the end 501.

Figure 23:
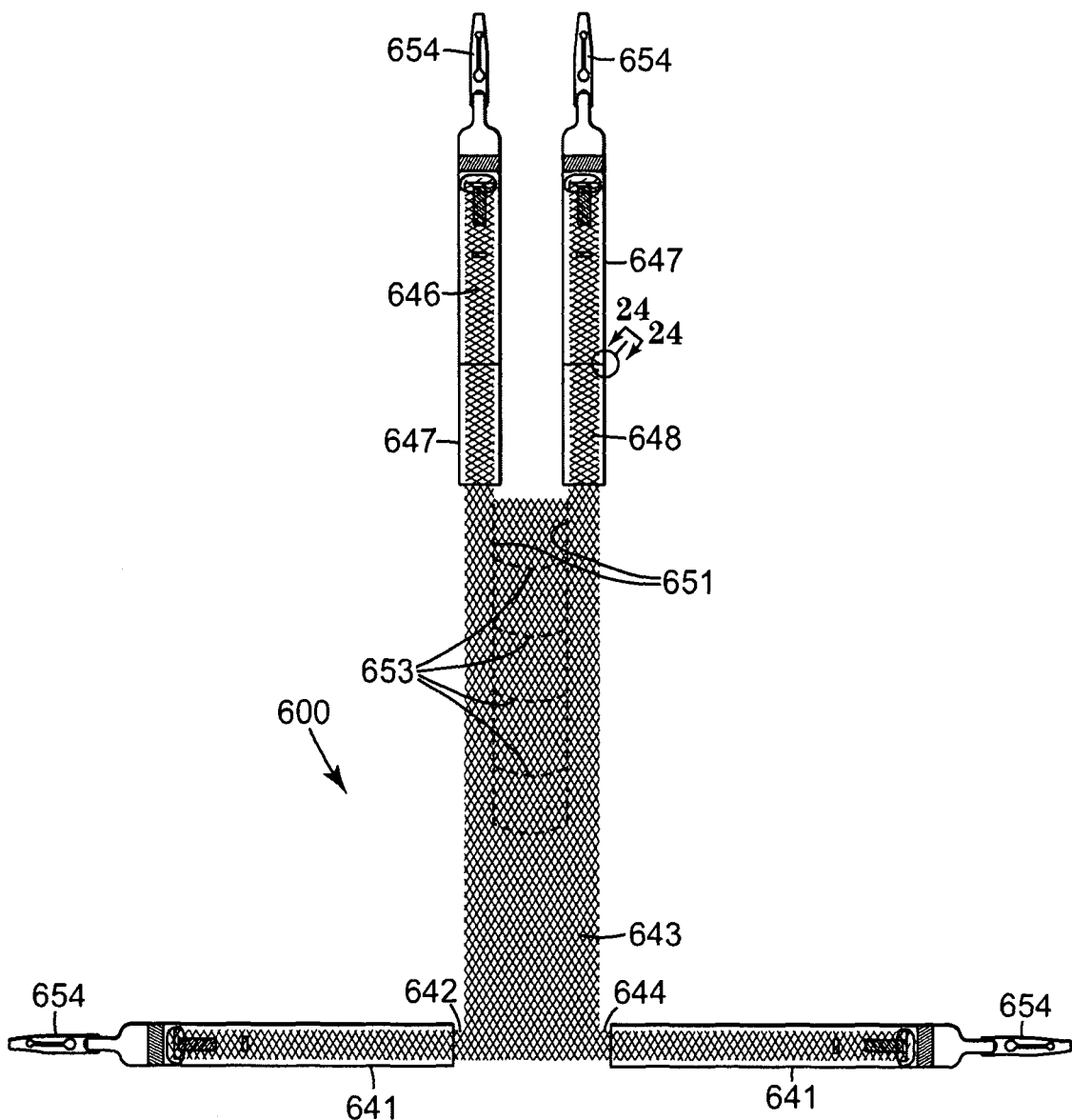
FIG. 23 is another embodiment of implant according to the present invention, which implant includes indicia to afford convenient trimming to a predetermined shape.
Figure 24:
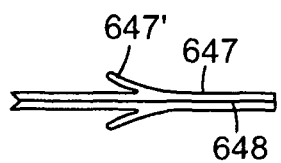
FIG. 24 is a side view of a portion of the implant of FIG. 23, taken approximately at lines 24-24 in FIG. 23.

FIGS. 23 and 24 show another embodiment of implant 600 according to the present invention. The implant includes sling appendages 642 and 644 and optional dilators 654. The appendages may be curved or substantially rectangular (as shown) and may project from a major portion 643 of the material at an angle between 0 and 90 degrees. The implant 600 also has posterior securement appendages 646 and 648.

The implant 600 has indicia 651 and 653 that allow the implant to be used in a universal manner. The implant may be trimmed along the indicia 651 to address different sizes of cystocele, or rectocele and different anatomy sizes. In addition to a trimming pattern, the indicia can include measurement marking (e.g. cm distances) to assist the surgeon in trimming the implant to its desired size and shape. For example, for a small anatomy or a small cystocele, the surgeon may trim along lines 651 and cut out a portion of the central part 643 of the implant. The surgeon need not trim along transverse indicia 653. Instead, the surgeon may trim along lines 651 and use the portion of the implant between the trims for a rectocele repair.

The implant preferably includes insertion sheaths 647 and 641. Referring to FIG. 24, the sheaths 647 preferably comprise an extendable member that can be movable from i) a retracted position with a portion of the sheath Z-folded as shown in FIG. 24, to ii) an extended position with additional of the material of the implant covered by the sheath. This is particularly useful when the portion of the implant along indicia 651 and 653 is removed. It is believed that extending the sheath over additional parts of the implant may afford a more convenient insertion of this portion of the implant. An extendable sheath may be accomplished in a variety of fashions including Z-folding the sheath, constructing the sheath of a stretchable or expandable material, and the like.

Examples of Materials

Figure 25:
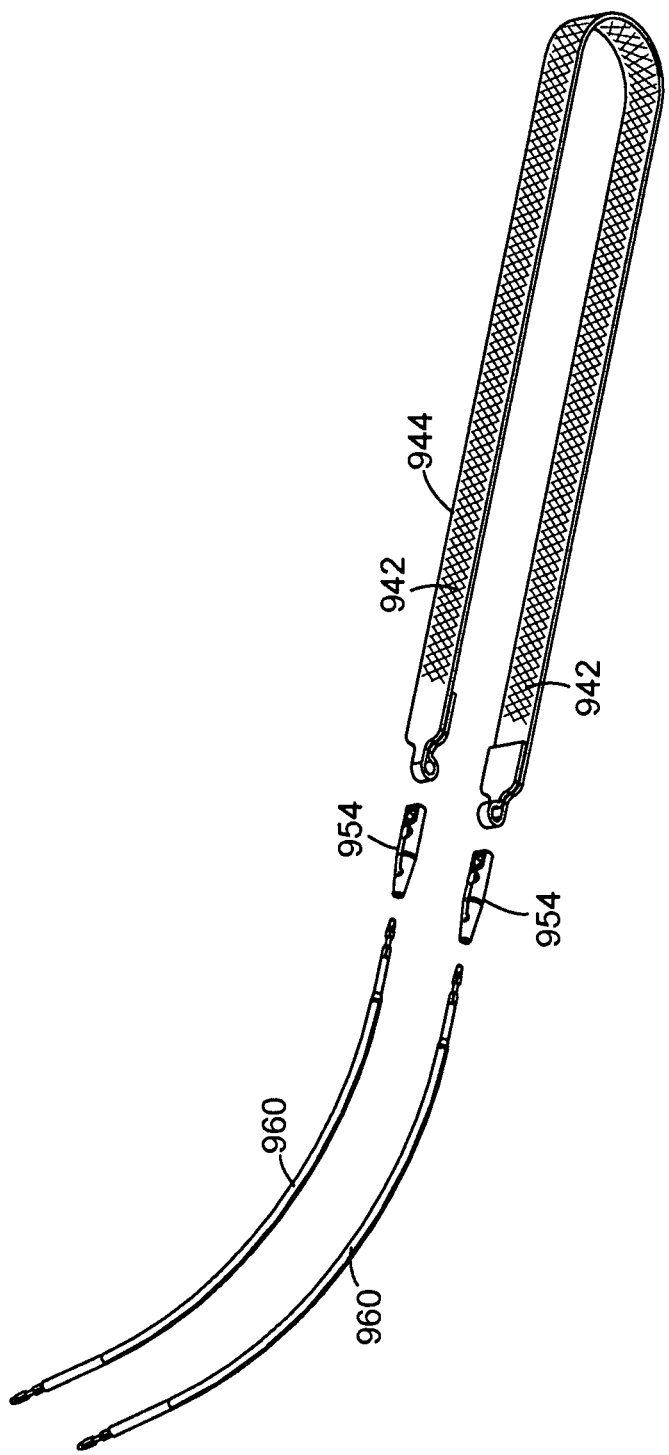
FIG. 25 is a perspective view of a novel assembly for addressing vaginal vault prolapse that includes a longitudinally extendable sling.

In one aspect, the present invention comprises a longitudinally extendable synthetic material in an implant secured in a posterior region of the body. For example, the implant of FIG. 25 is a rectangular implant that may be sutured or otherwise associated with the vaginal region (e.g. the vaginal apex) to address vaginal vault prolapse or to support the vault. Preferably, distal end regions 942 of the implant are secured in the ischioanal fossa or ischiorectal fossa of the patient's buttocks. The length of this embodiment is preferably between 25 and 45 cm, more preferably between 30 and 40 cm. The width is preferably between 0.5 cm and 1.5 cm, more preferably about 1 cm. The bulk synthetic may be knitted, woven, sprayed or punched from a blank.

Preferably, longitudinally extendible implants have an associated removable insertion sheath or sleeve (e.g. 47 in FIG. 3 or 944 in FIG. 25). The sheath is preferably made of polyethylene and is substantially transparent or translucent. Other materials include without limitation, polypropylene, nylon, polyester or PTFE (polytetrafluoroethylene, Teflon). The sheath material should be flexible and provide sufficient structural integrity to withstand the various forces exerted on the sheath throughout the implant delivery procedure. The sheath should also conveniently separate from a knitted implant material after the implant is implanted without materially changing the position of the implant in vitro.

As Sample A (see below), a mesh included polypropylene monofilaments, knitted with a warp tricot. The stitch count was 27.5 courses/inch (+ or −2 courses) and 13 wales/inch (+ or −2 wales). The thickness of this example is 0.024 inches. The average flexural rigidity was about 257.8 (g-cm). The fiber size was about 0.0046 inches. The average mesh density (in g/cm$^3$) was about 0.125. In Sample A, the holes comprised polygonal shaped holes with diagonals of 0.132 inches and 0.076 inches. A sample of this bulk material is available in the SPARC Sling System, commercially available from American Medical Systems of Minnetonka, Minn.

Figure 21:
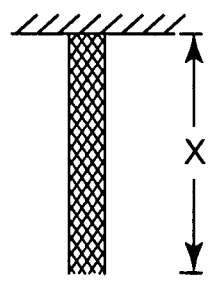
FIG. 21 is a schematic view of the initial length of a piece of bulk material, which view helps describe a test for determining a material's Longitudinal Elongation Factor.

A test may be conducted on a 0.8 mm by 3 inch sample of a bulk material to determine its Longitudinal Extensibility Factor (LEF) under different loads. The test may utilize a series IX Automated Materials Testing System (an Instron), available from Instron Corporation. An 8 mm wide sample of the mesh may be placed in the Instron with a crosshead speed set at 5 in/min. The 3 inch test sample is inserted to provide a gauge length of 1 inch. Referring to FIG. 21, the length X is 1 inch.

Figure 22:
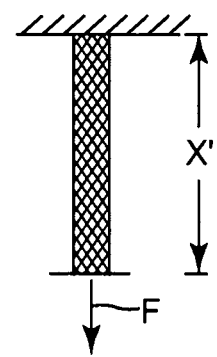
FIG. 22 is a schematic side view of a force being applied to the material of FIG. 21, and showing an elongation distance.

Referring to FIG. 21, the bulk mesh material may be subjected to various loads F. The amount that the sample increases in length X' under the load F is shown in FIG. 22.

The above identified test was conducted on three separate samples. The first sample (Prior Art) was an 8 mm×3 inch prior art sample obtained from the material provided with the IVS Tunneler product. Sample A was an ethylene oxide sterilized mesh as described above. Sample B comprised a 0.8 mm×3 inch sample of a Prolene Mesh, which is a knitted polypropylene monofilament mesh, commercially available from Ethicon of New Jersey. Sample B was tested both longitudinally and a direction perpendicular to the longitudinal direction.

Figure 28A:
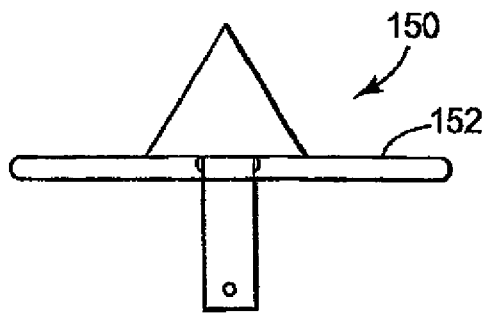
FIG. 28a is a side view of another embodiment of anchor according to the present invention, showing the anchor in a deployed position.
Figure 28B:
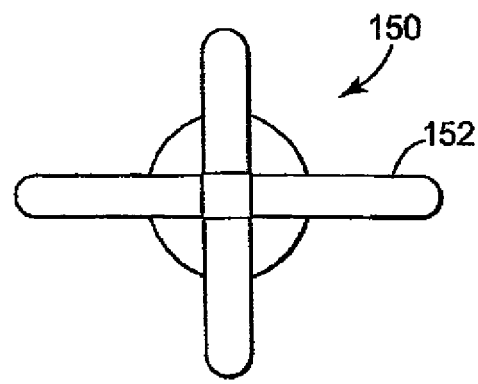
Figure 28C:
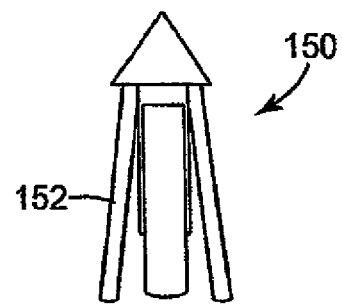
FIG. 28c is a side view of the anchor of FIG. 28a, showing the anchor in a pre-deployment position.

FIGS. 28a-c show another embodiment of deployable member 150 according to the present invention. The deployable member 150 includes a shaft, and a pointed top to assist in piercing tissue. Preferably, this portion is constructed of a biocompatible, bioabsorbable material. The deployable member 150 also includes a plurality of movable arms 152. These elements are preferably construed from a substantially permanent material (e.g. Delrin, Teflon, or Nylon). The arms 152 may comprise living hinges associated with the shaft or the member 150.

FIG. 29 illustrates a sling 43 preferably having a tension adjustment or control member 66 associated with the sling 43, for transferring sling adjustment forces from one portion of the sling 43 to another portions of the sling 43 such as the ends 61 of a support portion of the sling. The member 66 affords effective repositioning of the sling 43 while avoiding undesirable permanent deformation of the sling 43.

Table 1 includes test results conducted on the Prior Art, and Samples A and B.

| | Longitudinal Elongation Factor Elongation (in/in of length) @ various loads (lbf) | | | | | Load at |
|---|---|---|---|---|---|---|
| Sample # | 0.5 lbf | 1.0 lbf | 1.5 lbf | 2.0 lbf | Disp. At Max. Load | Max Load (lbf) |
| Prior Art | 0.05 | 0.07 | 0.090 | 0.11 | 0.434 | 10.58 |
| A | 0.17 | 0.23 | 0.28 | 0.33 | 1.267 | 12.96 |
| B longitudinally | 0.35 | 0.53 | 0.61 | 0.74 | 1.2 | 6.86 |
| B Perpendicular to Long. Axis | 0.082 | 0.17 | 0.28 | 0.37 | 0.80 | 12.43 |

A longitudinally extensible mesh exhibits at least a Longitudinal Elongation Factor (LEF) of 0.06 under a ½ pound load, more preferably a LEF of more than about 0.08 under a ½ pound load, and more preferably a LEF of more than about 0.15 under a ½ pound load. A longitudinally extensible mesh exhibits a LEF of at least 0.08 under a 1 pound load, more preferably a LEF of more than about 0.1 under a 1 pound load, and more preferably an LEF of more than about 0.2 under a 1 pound load. Additional results may be seen in the table.

In contrast, the longitudinally inextensible mesh associated with the IVS Tunneller device exhibited an LEF of less than 0.05 under a ½ pound load, and less than 0.07 under a 1 pound load.

Bulk mesh materials used to create Samples A and B may be cut into any of a wide variety of shapes, including those shown in the figures of this application and others. For example, a simple rectangular shape may be utilized with dimensions of about 1 inch×about 6 inches. In this example, the mid region of the rectangle could be sutured to the vagina (e.g. in the vaginal apex region) and the ends of the longitudinally extendible material may be secured in the patient's ischioanal fossa or ischiorectal fossa.

Examples of Surgical Procedures

Several methods are contemplated herein. Although the methods of use as disclosed herein generally relate to female prolapse conditions and treatments/procedures, incontinence conditions and treatments/procedures are also included within the scope of the present invention.

A variety of different surgical approaches are contemplated herein including a supra-pubic (i.e. the distal end of a needle initially being inserted through an abdominal incision and then emerging from a vaginal incision), trans vaginal (the distal end of an insertion needle being initially inserted through a vaginal incision and then emerging from an abdominal incision), trans-obturator (e.g. the distal end of a needle initially being inserted through an incision in skin near the patient's obturator foramen and then emerging from a vaginal incision or vice versa) and posterior approaches. Preferably, the implants according to the present invention are inserted through a vaginal incision. Alternative insertion routes such as laparoscopic and through an open abdominal incision are also within the scope of the present invention.

It should be noted that the present invention is particularly suitable for placing an implant in a therapeutically effective position. The method may be utilized to support a variety of structures at different anatomical locations. Variations of these methods may occur due to individual surgeon's techniques or a patient's particular anatomy. For example, the amount of dissection employed varies greatly between surgeons and procedures. As another example, the particular order in which the elements of the implant are secured are also within the individual surgeon's discretion. Some surgeons may initially place a cystocele repair portion of an implant and then secure sling appendages. Others may initially place sling appendages and then secure a cystocele portion of the implant. As yet another example, some surgeons may elect to secure an implant to the vaginal cuff or apex, other surgeons may elect to place sutures through the implant and a portion of the posterior or anterior wall of the vagina.

As another example, there are a variety of different methods of attaching an implant in the vaginal region for purposes of vaginal vault support or correction of vaginal vault prolapse. Some surgeons may suture a mid region of a rectangular mesh to the vaginal region (e.g. apex). This is preferably conducted without traversing through vaginal mucosa.

In embodiments of the present invention that include sling appendages, the sling appendages are preferably implanted mid-urethra in a tension free manner. Preferably the implant is slightly spaced from the urethra. Also preferably, in embodiments of implants that include a cystocele repair portion, the implant is secured in a tension free manner without traction on the bladder.

Figure 7:
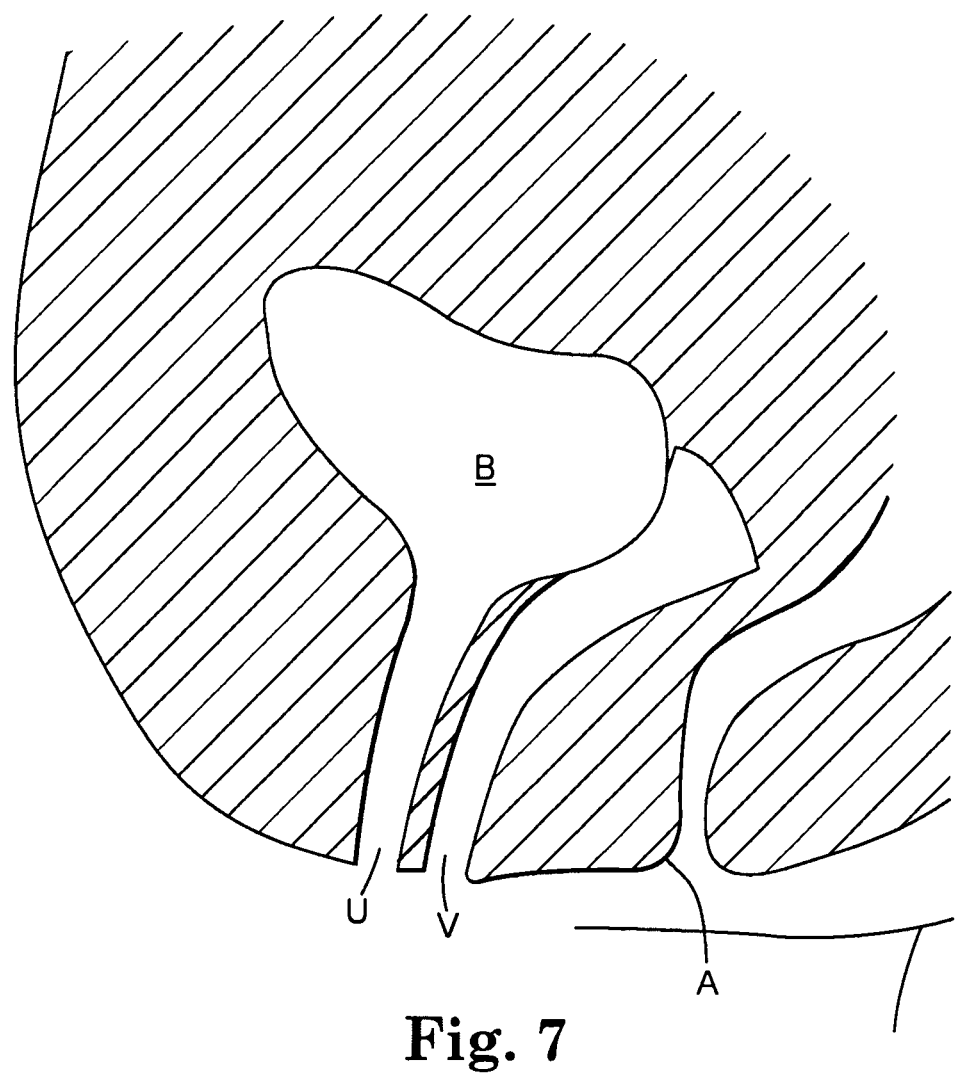
FIG. 7 is a schematic view illustrating a cystocele.

FIG. 7 schematically illustrates a patient's anatomy including the bladder B, urethra U, vagina V and anus A. The bladder B is shown slightly prolapsed into the vagina V. Often such patents exhibit stress urinary incontinence.

Figure 8:
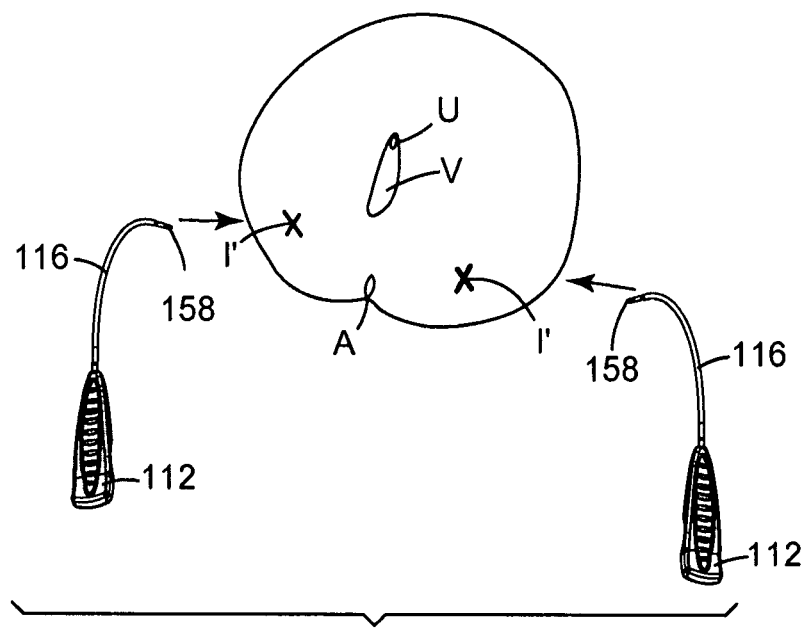

Referring to FIGS. 8 through 13 schematically illustrate a procedure for addressing vaginal prolapse through a posterior surgical approach. Referring to FIG. 8, in contrast to some prior art surgical procedures, a kit according to the present invention utilizes two, independent sterile needles 116. Preferably, the needles 116 utilize handles 112 and have distal ends 158.

Figure 9:
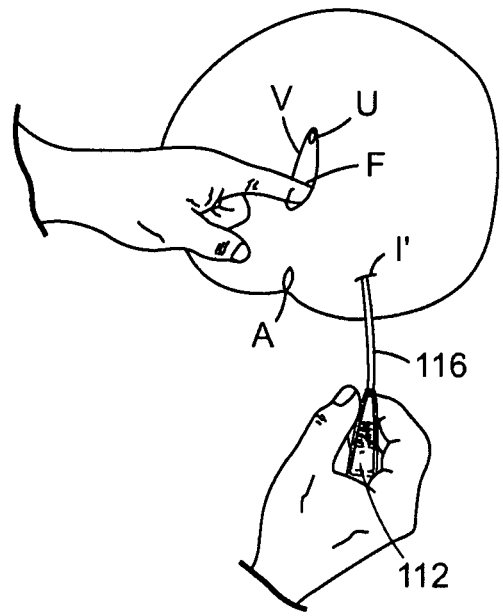
Figure 11:
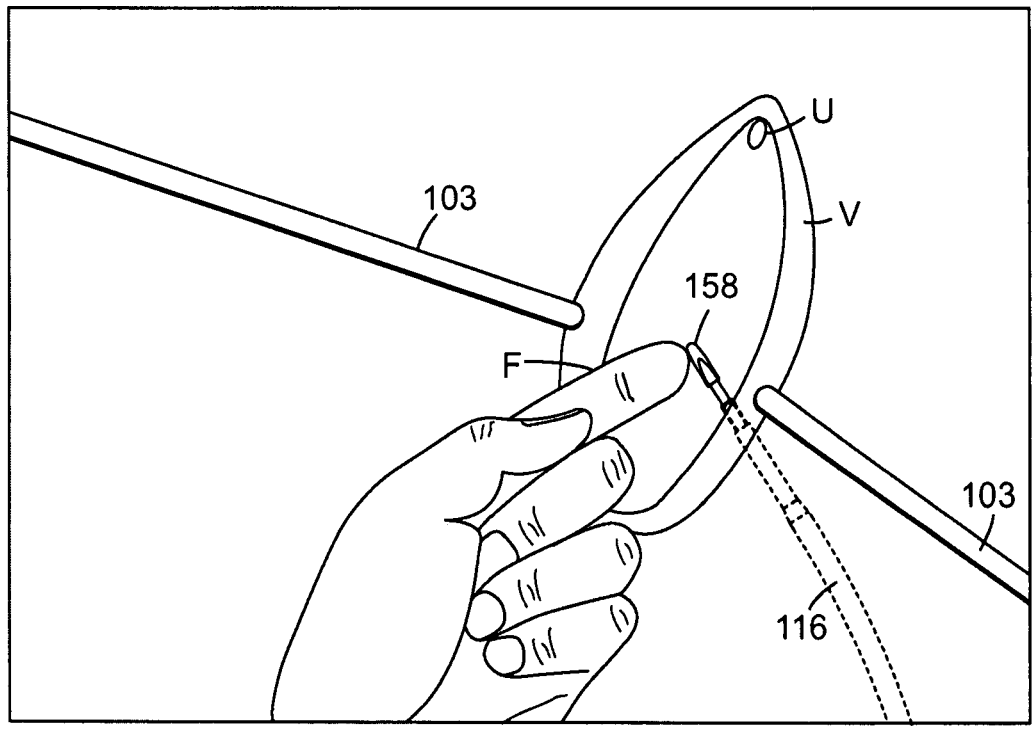

Incisions I' are placed laterally on each side of the anus A. Preferably, the incisions are placed proximate the patient's ischioanal fossa or ischiorectal fossa. Referring to FIG. 9, a needle 116 is passed initially through the incision I' and is guided to meet the surgeon's finger F. FIG. 11 shows the distal end 158 of the needle 116 meeting the surgeon's finger F exposed by retractors 103.

Figure 10:
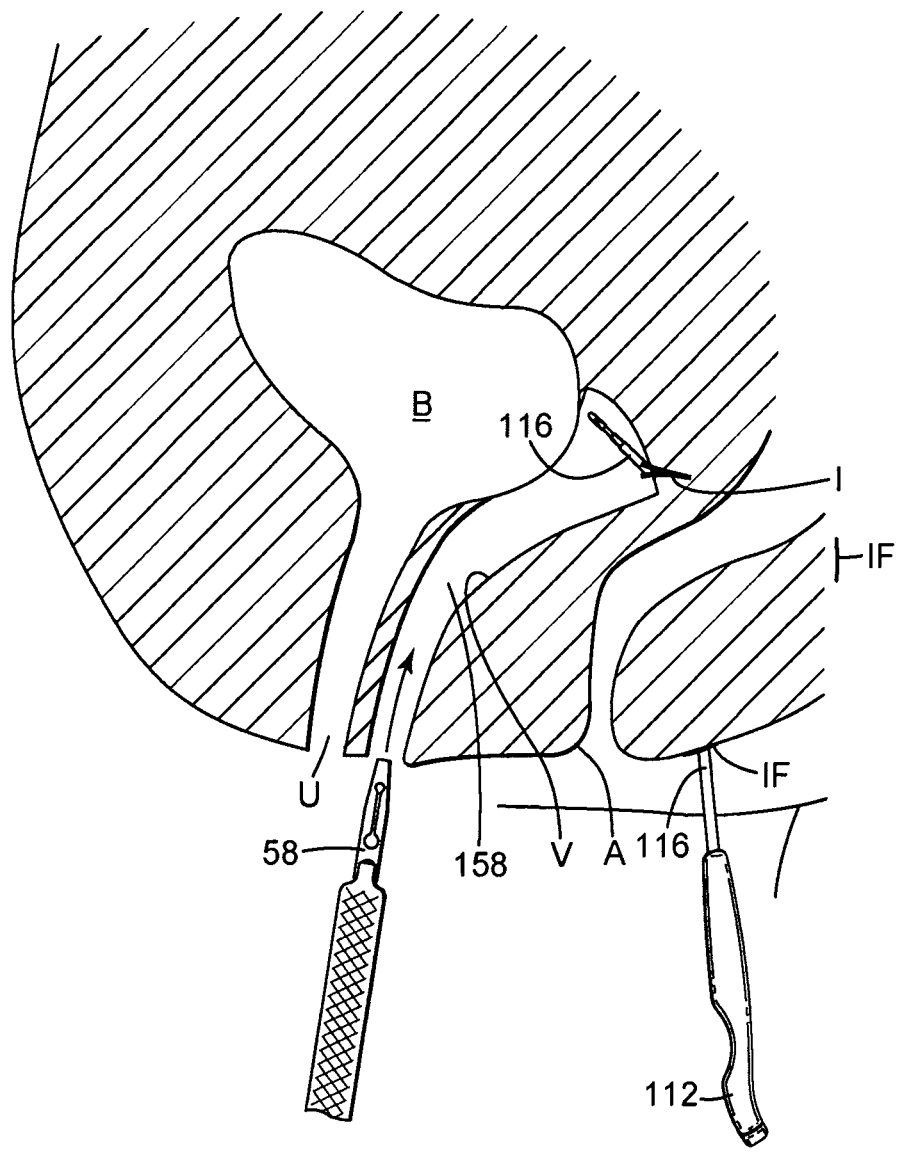
Figure 12:
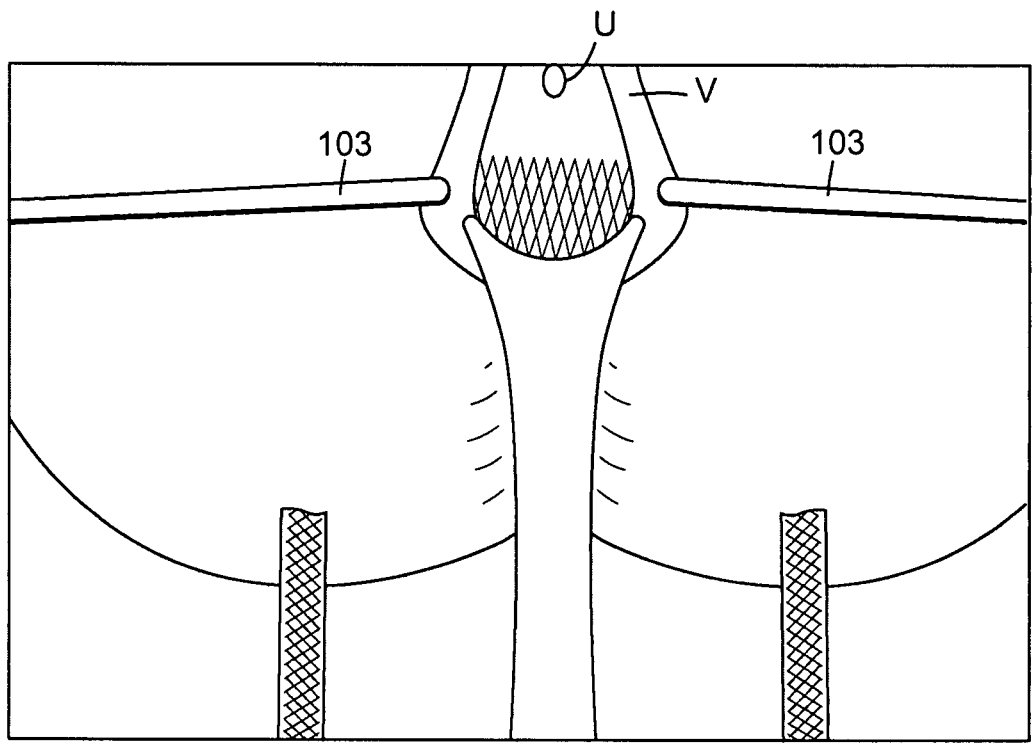

FIG. 10 shows the distal end 158 of the needle 116 after it emerges from an incision I in the vaginal region (e.g. in the region of the vaginal apex or cuff). A dilator 58 (in this case associated with the implant and an insertion sheath) is then attached to the distal end of the needle. In this case, the implant may simply be a rectangular, longitudinally extendible implant and insertion sheath. To correct a vaginal prolapse with such an implant, the mid portion may be sutured to the vagina (e.g. in the vaginal cuff region) via the incision I. Then the distal ends of the implant may be connected to the distal ends 158 of the needles 116 and moved from the vaginal region through the ischioanal fossa or ischiorectal fossa IF and appropriately tensioned. FIG. 12 shows the distal ends of the mesh projecting through incisions in the buttocks. The insertion sheaths are then removed from the implant. Optional tensioning sutures in the mesh may optimally be provided to fine tune the final placement of the mesh. Tensioning sutures may also afford adjustment of implant position in the immediate post operative period. Preferably, the vagina is secured in a tension free manner.

Figure 13:
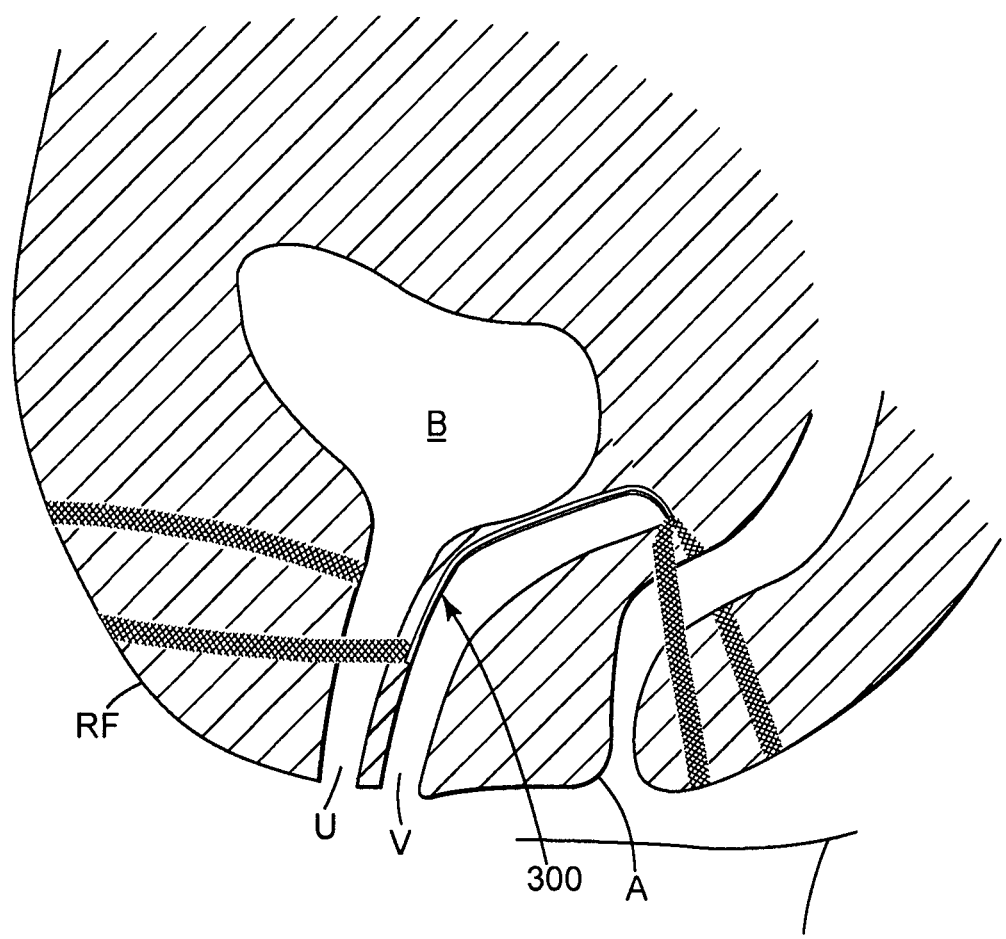

FIG. 13 illustrates placement of a more complex mesh shape according to the present invention. In this embodiment, two appendages of the implant 300 are passed suprapubically to provide sling like support to the urethra to address incontinence, and two other appendages are passed posteriorly through ischioanal fossa or ischiorectal fossa to secure the implant 300. Notably, the implant 300 simultaneously addresses incontinence and prolapse.

All patents, patent applications, and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating a pelvic condition, the method comprising
   providing an implant comprising
      a synthetic mesh material having a central portion adapted to be secured in the patient's vaginal region,
      a first posterior securement appendage extending from the central portion and that is sized, shaped, and configured to extend from the patient's vaginal region and be anchored to the patient's sacrospinous ligament;
      a second posterior securement appendage extending from the central portion and that is sized, shaped, and configured to extend from the patient's vaginal region, on a side of the patient different than that of the first posterior securement appendage, to be anchored to the patient's sacrospinous ligament,
   positioning the central portion, in the patient's vaginal region,
   extending and anchoring the first posterior securement appendage to the patient's sacrospinous ligament, and
   extending and anchoring the second posterior securement appendage to the patient's sacrospinous ligament on a side of the patient different than that of the first posterior securement appendage.

2. A method according to claim 1 comprising a sacral colpopexy.

3. A method according to claim 1 comprising treating vaginal vault prolapse.

4. A method according to claim 1 wherein the implant is placed transvaginally.

5. A method according to claim 1 wherein the method is performed laparoscopically.

* * * * *